(12) United States Patent
Lehman et al.

(10) Patent No.: US 6,635,245 B1
(45) Date of Patent: Oct. 21, 2003

(54) STRAIN OF BACILLUS FOR CONTROLLING PLANT DISEASES

(75) Inventors: Lori Jo Lehman, Vacavilla, CA (US); Randy J. McCoy, Davis, CA (US); Belinda Jane Messenger, Davis, CA (US); Denise Carol Manker, Davis, CA (US); Jimmy Ensio Orjala, Davis, CA (US); Dorte Lindhard, Davis, CA (US); Pamela Gail Marrone, Davis, CA (US); Desmond Rito Jimenez, Woodland, CA (US)

(73) Assignee: AgraQuest, Inc., Davis, CA (US)

( * ) Notice: Subject to any disclaimer, the term of this patent is extended or adjusted under 35 U.S.C. 154(b) by 0 days.

(21) Appl. No.: 09/532,021

(22) Filed: Mar. 21, 2000

Related U.S. Application Data (63) Continuation-in-part of application No. 09/281,360, filed on Mar. 30, 1999, now Pat. No. 6,245,551, which is a continuation-in-part of application No. 09/461,700, filed on Dec. 14, 1999.

(51) Int. Cl.$^7$ .............................................. A01N 63/00
(52) U.S. Cl. ............................... 424/93.46; 435/252.4; 435/252.5; 504/117
(58) Field of Search ........................ 435/252.5, 252.4; 424/93.45; 504/117

(56) References Cited

U.S. PATENT DOCUMENTS

| | | |
|---|---|---|
| 4,250,170 A | 2/1981 | Kawaguchi et al. |
| 4,448,885 A | 5/1984 | Schnepf et al. |
| 4,467,036 A | 8/1984 | Schnepf et al. |
| 4,797,276 A | 1/1989 | Herrnstadt et al. |
| 4,849,217 A | 7/1989 | Soares et al. |
| 4,853,331 A | 8/1989 | Herrnstadt et al. |
| 4,918,006 A | 4/1990 | Ellar et al. |
| 4,948,734 A | 8/1990 | Edwards et al. |
| 4,966,765 A | 10/1990 | Payne et al. |
| 4,990,332 A | 2/1991 | Payne et al. |
| 4,996,155 A | 2/1991 | Sick et al. |
| 4,999,192 A | 3/1991 | Payne et al. |
| 5,006,336 A | 4/1991 | Payne et al. |
| 5,024,837 A | 6/1991 | Donovan et al. |
| 5,045,469 A | 9/1991 | Payne et al. |
| 5,047,239 A | 9/1991 | Pusey |
| 5,049,379 A | 9/1991 | Handelsman et al. |
| 5,055,294 A | 10/1991 | Gilroy |
| 5,061,495 A | 10/1991 | Rossall |
| 5,063,055 A | 11/1991 | Burges et al. |
| 5,073,632 A | 12/1991 | Donovan |
| 5,080,897 A | 1/1992 | Gonzalez, Jr. et al. |
| 5,093,119 A | 3/1992 | Hickle et al. |
| 5,106,620 A | 4/1992 | Hickle et al. |
| 5,126,133 A | 6/1992 | Payne et al. |
| 5,128,130 A | 7/1992 | Gilroy et al. |
| 5,135,867 A | 8/1992 | Payne et al. |
| 5,147,640 A | 9/1992 | Gard, Jr. et al. |
| 5,151,363 A | 9/1992 | Payne |
| 5,164,180 A | 11/1992 | Payne et al. |
| 5,173,409 A | 12/1992 | English |
| 5,185,148 A | 2/1993 | Michaels |
| 5,186,934 A | 2/1993 | Narva et al. |
| 5,187,091 A | 2/1993 | Donovan et al. |
| 5,196,342 A | 3/1993 | Donovan |
| 5,208,017 A | 5/1993 | Bradfisch et al. |
| 5,211,946 A | 5/1993 | Payne et al. |
| 5,344,647 A | 9/1994 | Rossall |
| 5,403,583 A | 4/1995 | Liu et al. |
| 5,597,565 A | 1/1997 | Leifert et al. |
| 5,702,703 A | 12/1997 | Schnepf et al. |
| 5,780,080 A | 7/1998 | Leifert et al. |
| 6,103,228 A * | 8/2000 | Heins ..................... 424/93.46 |
| 6,245,551 B1 * | 6/2001 | Lehman ................... 435/252.5 |

FOREIGN PATENT DOCUMENTS

| | | |
|---|---|---|
| DE | 293482 | 9/1991 |
| SU | 1817875 | 5/1995 |
| WO | WO 93 18654 | 9/1993 |
| WO | WO 96/10083 | 4/1996 |
| WO | WO 96/39037 | 12/1996 |

OTHER PUBLICATIONS

B'Chir, M.M. and Belkadhi, M.S., "Nouvelles donnees sur les modifications histologiques induites par le complexe Fusarium solani—Tylenchulus semipenetrans au niveau des racines de portes–greffes de citrus" *Med. Fac. Landbouww. Rijksuniv. Gent* 51(3b):1295–1310 (1986) English Abstract.

B'Chir, M.M. and Namouchi, N. "Effet de *Bacillus pimulus* sur *Monacrosporium salinium*, un champignon prédateur de nématodes" *Revue Nématol.* 11(2):263–266 (1988) English Abstract.

Baker et al., "Inhibitory effect of *Bacillus subtilis* on *Uromyces phaseoli* and on development of rust pustules on bean leaves" *Phytopathol.* 73:1148–1152 (1983).

Cook, C.G. et al., "Effect of Treatment With Bacillus Species on Cotton Root Traits, Yield, and Phymatotrichum Root Rot" *Beltwide Cotton Production Research Conferences*, 1987 Proceedings, Jan. 4–8, 1987, Dallas, Texas, pp. 43–45 (1987).

Ferreira et al., "Biological control of *Eutypa lata* on grapevine by an antagonistic strain of *Bacillus subtilis*" *Phytopathology* 81:283–287 (1991).

Gokte, N. and Swarup, G. "On the Association of Bacteria with Larvae and Galls of *Anguina tritici*" *Indian J. Nematol.* 18(2):313–318 (1988).

(List continued on next page.)

*Primary Examiner*—Irene Marx
(74) *Attorney, Agent, or Firm*—Morrison & Foerster LLP (57) ABSTRACT

A novel antibiotic-producing Bacillus sp. is provided that exhibits antifungal activity only on certain specific plant pathogens and no antibacterial activity is provided by this invention, as well as a biologically pure culture of a strain having all the identifying characteristics of this strain. Also provided is a method of treating or protecting plants, fruit and roots from fungal infections by applying an effective amount of these strains, supernatants produced by these strains or a metabolite isolated from these strains. The invention further encompasses the synergistic fungicidal effect of using a strain of NRRL Accession Nos. B-30087 together with B-21661 (AQ 713).

15 Claims, 6 Drawing Sheets

OTHER PUBLICATIONS

He et al., "Zwittermycin A, an antifungal and plant protection agent from *Bacillus cereus*" *Tetrahedron Lett.* 35(16):2499–2502 (1994).

Islam, K.Z. and Nandi, B., "Control of brown spot of rice by *Bacillus megaterium*" *J. Plant Dis. Protect.* 92(3):241–246 (1985).

Islam, K.Z. and Nandi, B., "Inhibition of some fungal pathogens of host phylloplane by *Bacillus megaterium*" *J. Plant Dis. Protect.* 92(3):233–240 (1985).

Korzybski, T. et al., "Section C: Antibiotics isolated from the genus Bacillus (Bacillaceae)" In: Antibiotics—Origin, Nature and Properties, American Society for Microbiology, Washington, D.C. 1978, Vol III, pp. 1529–1661 (1978).

Leifert et al., "Antibiotic production and biocontrol activity of *Bacillus subtilis* CL27 and *Bacillus pumilus* CL45" *J. Appl. Bacteriol.* 78:97–108 (1995).

Loeffler, W. et al., "Antifungal Effects of Bacilysin and Fengymycin from *Bacillus subtilis* F–29–3. A Comparison with Activities of Other Bacillus Antibiotics" *J. Phytopathol.* 115:204–213 (1986).

McInroy, J.A. and Kloepper, J.W., "Survey of indigenous bacterial endophytes from cotton and sweet corn" Plant and Soil 173(2):337–342 (1995).

McKeen et al., "Production and partial characterization of antifungal substances antagonistic to *Monilinia fructicola* from *Bacillus subtilis*" Phytopathology 76:136–139 (1986).

Milner et al., "Production of Kanosamine by *Bacillus cereus* UW85" *Appl. Environ. Microb.* 62:3061–3065 (1996).

Osburn et al., "Effect of *Bacillus cereus* UW85 on the yield of soybean at two field sites in Wisconsin" *Am. Phytopathol. Soc.* 79(6):551–556 (1995).

Pusey et al., "Pilot tests for commercial production and application of *Bacillus subtilis* (B–3) for postharvest control of peach brown rot" *Plant Dis.* 72:622–626 (1988).

Schwinn et al., "Control with Chemicals" in: Advances In Plant Pathology: Phytophthora Infestans, The Cause of Late Blight of Potato, vol. 7, Academic Press, San Diego, CA, p. 244 (1991).

Sholberg et al., "Biocontrol of postharvest diseases of apple using Bacillus spp. isolated from stored apples" *Can. J. Microbiol.* 41:247–252 (1995).

Singh, V. and Deverall, B.J., "*Bacillus subtilis* as a control agent against fungal pathogens of citrus fruit" *Trans. Br. Mycol. Soc.* 83:487–490 (1984).

Slabospitskaya, A.T. and Krymovskaya, S.S., "Chitinases of Aerobic Spore–Forming Bacteria Isolated from Different Ecological Sources" *Mikrobiol. Zh. (Kiev)* 54(6):16–22 (1992) Abstract in English.

Stabb et al., "Zwittermycin A–producing strains of *Bacillus cereus* from diverse soils" *Appl. Environ. Microbiol.* 60:4404–4412 (1994).

Swinburne et al., "Production of antibiotics by *Bacillus subtilis* and their effect on fungal colonists of apple leaf scars" *Trans. Brit. Mycol. Soc.* 65:211–217 (1975).

Tsuno et al., "3,3'–Neotrehalosadiamine (BMY–28251), A New Aminosugar Antibiotic" *J. Antibiotics* XXXIX(7):1001–1003 (Jul. 1986).

Argauer et al., "Evidence for a novel insecticidally active exotoxin produced by the HD 116 strain of *Bacillus thuringiensis* var. *morrisoni*" *J. Entomol Sci.* 26(2):205–213 (1991).

Burgerjon, A. and Biache, G. "Alimentation au laboratoire de *Perillus bioculatus* Fabr. avec des larves de *Leptinotarsa decemlineata* intoxiquées par la toxine thermostable de *Bacillus thuringiensis* Berliner" *Entomophaga* 11:279–284 (1979). An English summary is contained on p. 283.

Estruch et al., "Transgenic plants: An emerging approach to pest control" *Nature Biotechnol.* 15:137–141 (1997).

Forsberg, C.W., in: *Bacillus thuringiensis*: Its Effects on Environmental Quality, National Research Council of Canada, Publication No. NRCC 15385, pp. 91–109 (1976).

Gaertner, F. and Kim, L., "Current Applied Recombinant DNA Projects" *TIBTECH* 6(4):S4–S7 (Apr. 1988).

Johnson et al., "Insecticidal activity of EG4961, a novel strain of *Bacillus thuringiensis* toxic to larvae and adults of Southern corn rootworm (Coleoptera: Chrysomelidae) and Colorado potato beetle (Coleoptera: Chrysomelidae)" *J. Econ. Entomol.* 86:330–333 (1993).

Lüthy, "Insecticidal toxins of *Bacillus thuringiensis*" *FEMS Microbiol. Lett.* 8:1–7 (1980).

Marrone et al., "Improvements in laboratory rearing of the Southern corn rootworm, *Diabrotica undecimpuncta howardi barber* (Coleoptera: Chrysomelidae), on an artificial diet and corn" *J. Econ. Entomol.* 78:290–293 (1985).

Schnepf, H.E. and Whiteley, H.R., "Cloning and expression of the *Bacillus thuringiensis* crystal protein gene in *Escherichia coli*" *Proc. Natl. Acad. Sci. USA* 78(5):2893–2897 (May 1981).

Stonard et al., "Microbial secondary metabolites as a source of agrochemicals" *ACS Symposium Series*, Chapter 3, pp. 25–36 (1994).

Asano, et al., "Prodigiosin Produced by *Serratia marcescens* Enhances the Insecticidal Activity of *Bacillus thuringiensis* delta Endotoxin (Cry1C) against Common Cutworm, *Spodoptera litura*" J. Pesticide Sci, (1999) 24: 381–385.

Asano, et al., Appl. Entomol. Zool. (2000), 35 (4), 575–582.

Hori, et al., "Fractionation and Some Features of Synergistic Compounds Which Enhances the Insecticidal Activity of δ–Endotoxin of *Bacillus thuringiensis*", Appl. Entomol. Zoology, (1996) 31 (1): 29–35.

Kelada, et al., "Toxicity of Three Chemical Insecticides in Combination with Bacillus spp. Against Mosquito Larvae" Insect Sci. Appl. (1988) 9(2): 229–231.

Pramanik, et al., "Persistence Toxicity of *Bacillus thuringiensis* Var Kurstaki in Combination with some Chemical Additives Under Field Condition" Environ. Ecology(2000) 18(1): 114–118.

Salama, et al., "Possible extension of the activity spectrum of *Bacillus thuringiensis* strains through chemical additives" J. Appl. Ent. (1986) 101 304–13.

Sivamani, et al., "Influence of some plant phenolics on the activity of δ–Endotoxin of *Bacillus thuringiensis* var. *galleriae* on *Heliothis armigera*" Entomol. Exp. Appl. (1992) 63: 243–8.

Swadling, I. R. et al., Antagonistic Properties of Two Bacterial Biocontrol Agents of Grey Mould Disease; Biocontrol Science and Technology: vol. 8. 3, 1998, pp. 439–448.

Ellar, D.J. "The Structure and Function of *Bacillus Thuringiensis* Endotoxins and Prospects for Biopesticide Improvement", 1997 BCPC Symposium Proceedings No. 68: Microbial Insecticides: Novelty or Necessity?, pp. 83–100.

* cited by examiner

STRAIN OF BACILLUS FOR CONTROLLING PLANT DISEASES

This application is a continuation-in-part of U.S. Ser. No. 09/281,360, filed Mar. 30, 1999, now U.S. Pat. No. 6,245,551 B1, issued Jun. 12, 2001, which in turn is a continuation-in-part of U.S. Ser. No. 09/461,700, filed Dec. 14, 1999, the contents of which are hereby incorporated by reference into the present disclosure.

FIELD OF THE INVENTION

The present invention is in the field of biopesticides. More particularly, this invention relates to the finding that a novel strain of *Bacillus pumilus*, NRRL Accession Number B-30087, can inhibit a broad range of fungal plant diseases in vivo. The invention also relates to fungicidal compositions comprising this novel Bacillus strain, and the antibiotics and purified and non-purified fractions of this strain either alone, or in combination with other chemical and biological pesticides. The invention further relates to the synergistic fungicidal effect of using NRRL Accession No. B-30087 together with NRRL Accession No. B-21661, (CCRC 910106).

BACKGROUND

It is generally known that various microorganisms exhibit biological activity that are useful to control plant diseases. Although progress has been made in the field of identifying and developing biological pesticides for controlling various plant diseases of agronomic and horticultural importance, most of the pesticides in use are still synthetic compounds. Many of these chemical fungicides are classified as carcinogens by the Environmental Protection Agency (EPA), are toxic to wildlife and other non-target species. In addition, pathogens may develop resistance to chemical pesticides. See, e.g., Schwinn et al., in: Advances In Plant Pathology: *Phytopathora infestans*, The Cause of Late Blight of Potato, p. 244, Academic Press, San Diego, Calif. (1991).

Biological control offers an attractive alternative to synthetic chemical fungicides. Biopesticides (living organisms and the naturally produced compounds produced by these organisms) can be safer, more biodegradable, and less expensive to develop.

One commonly used biopesticide is the gram positive bacterium *Bacillus thuringiensis*. Pesticidal *B. thuringiensis* strains are known to produce crystal proteins during sporulation, which are specifically toxic to certain orders and species of insects and nematodes (See, e.g., U.S. Pat. No. 4,999,192 and U.S. Pat. No. 5,208,017). Proteinaceous endotoxins produced by *B. thuringiensis* also act as insecticidal agents against corn rootworm and other beetles (e.g., U.S. Pat. 5,187,09 and Johnson, T. J. et al. (1993), *J. Econ. Entomol.*, 86:330–333). *B. thuringiensis* endotoxins have been shown to be effective as purified crystals, washed cell pellets, and expressed proteins. Warren et al. WO 96/10083, disclose non-endotoxin proteins produced during the vegetative stage of *Bacillus cereus* and *B. thuringiensis*. These vegetative proteins, called Vip1 and Vip2 have potent activity against corn rootworm (northern and western). See, Estruch et al. (1997), *Nature-Biotechnology* 15:137–141.

One *B. thuringiensis* thermostable metabolite, termed beta-exotoxin has also been shown to have pesticidal properties. Burgjeron and Biache (1979), *Entomophaga* 11:279–284, report a beta-exotoxin that is active against Colorado potato beetle (*Leptinotarsa decemlineata*). In addition, the known *B. thuringiensis* beta-exotoxins exhibit non-specific pesticidal activity, not only killing nematodes, but also flies, armyworm, mites, and corn rootworm. Sigma exotoxin has a structure similar to beta-exotoxin, and is active against Colorado potato beetle. See, Argauer et al. (1991), *J. Entomol. Sci.* 26: 206–213. Alpha-exotoxin is toxic to larvae of *Musca domestica* (Cluthy (1980), *FEMS Microbiol. Lett.* 8:1–7). Gamma-exotoxins are various proteolytic enzymes, chitinases and proteases. The toxic effects of gamma-exotoxins are only expressed in combination with beta-exotoxin or delta-endotoxin. See, Forsberg, C., "*Bacillus thuringiensis*: Its effects on Environmental Quality" National Research Council of Canada, Publication No. NRCC 15385, pp. 91–109 (1976). Stonard et al. (1994), *ACS Symposium Series* 551:25, report a water-soluble secondary metabolite active against corn rootworm in the supernatant of a *Bacillus cereus* strain.

Zwittermicin A is a water soluble, acid stable linear arninopolyol molecule (see, He et al. (1994), *Tetrahedron Lett.* 35(16):2499–2502) with broad-spectrum activity against many fungal and bacterial plant pathogens. Zwittermicin A is also known to enhance the activity of *B. thuringiensis*. Manker et al. (WO 96/39037) were the first to determine the *B. thuringiensis*-enhancing abilities and properties of zwittermicin A. Subsequently, Schnepf et al. also reported that zwittermicin A enhanced *B. thuringiensis* (U.S. Pat. No. 5,702,703).

Bacilli are known to produce antifungal and antibacterial secondary metabolites. See, Korzybski et al. "Antibiotics isolated from the genus Bacillus (Bacillaceae)" in: Antibiotics—Origin, Nature and Properties, American Society for Microbiology, Washington, D.C. Vol. III (1978), and Berdy, CRC Handbook of Antibiotic Compounds, Vols. I–XIV, CRC Press, Inc., Boca Raton, Fla. (1980–87). Compounds produced by *B. pumilus* include micrococcin P, pumilin, and tetain.

Kawaguchi et al., in U.S. Pat. No. 4,250,170, isolated a novel water-soluble antibiotic from Bacillus with activity against a broad range of gram positive and gram negative bacteria. Stabb et al. (1990) *Applied Environ. Microbiol.* 60:4404–4412, have identified certain Bacillus spp. (Bacillus spp. include *B. subtilis, B. cereus, B. mycoides, B. thuringiensis*) strains that exhibit antifungal activity. These strains have been shown to produce zwittermicin A and/or kanosamine. See, Milner et al., *Appl. Environ. Microb.* 62:3061–3066 (1996). These are antibiotic agents that are effective against the soil borne disease damping off, caused by *Phytopathora medicaginis, P. nicotianae, P. aphanidermatum* or *Sclerotinia minor* (See, Stabb et al., supra). Zwittermicin-A is a water soluble, acid stable linear aminopolyol molecule. See, He et al., (1994) *Tetrahedron Lett.* 35(16):2499–2502. It has broad spectrum activity against many fungal and bacterial plant pathogens. Kanosamine (Milner et al., 1996) also inhibits a broad range of fungal plant pathogens and a few bacterial species.

Handelsman et al., in U.S. Pat. No. 5,049,379, describe how Zwittermicin A-producing *B. cereus* controls damping off in alfalfa and soybeans. When the seed was coated with *B. cereus* ATCC 53522, the pathogenic activity of root rot fungus was inhibited. Similarly, application of spore-based formulations of certain *B cereus* strains to soybean seeds or the soil surrounding the seeds has been shown to improve soybean yield at field sites. See, Osburne et al. (1995) *Am. Phytopathol. Soc.* 79(6):551–556. Methods of applying biopesticides are well known in the art and include, for example, wettable powders, dry flowables, microencapsulation, and liquid formulations of the microbe, whole broth or antibiotic fractions from suitable cultures.

See, e.g., U.S. Pat. No. 5,061,495 to Rossall and U.S. Pat. No. 5,049,379 to Handelsman et al.

Tsuno et al. (1986) *J. Antibiotics* XXXIX(7):1001–1003, report on a new amino sugar antibiotic from *B. pumilus* with activity against a broad range of bacteria in vitro.

Khmel, I. A. et al., (1995) in SU 1817875 disclose a novel strain of *Bacillus pumilus* VKM CR-333D, which is used to control fungal phytopathogens and bacteria.

Leifert et al., *J. Appl. Bacteriol.* 78:97–108 (1995), report the production of anti-Botrytis and anti-Alternaria antibiotics by two Bacillus strains, *B. subtilis* CL27 and *B. pumilus* CL 45. The whole broth and cell-free filtrates are active against Botrytis and Alternaria in in vitro tests and are active against Botrytis in in vivo small plant tests on Astilbe. Leifert et al. (1997) U.S. Pat. No. 5,597,565 disclose *B. subtilis, B. pumilus,* and *B. polymyxa* that are particularly effective at inhibiting post harvest disease causing fungi, *Alternaria brassicicola* and *Botrytis cinerea.* They also disclose the presence of antibiotics produced in the cell-free culture filtrate and their activity at different pH values, but they do not identify these compounds. The compounds from *B. subtilis* lose activity at low pH, while the activity from the *B. pumilus* extracts occurs only at pH values below 5.6. Leifert et al. (1998) U.S. Pat. No. 5,780,080 disclose cabbages that can be treated with *B subtilis, B pumilus,* and *B. polymyxa* strains to inhibit *Alternaria brassicicola* and *Botrytis cinerea.*

Loeffler et al. (1986) *J. Phytopathology* 115:204–213, disclose *B. subtilis, B. pumilus, B. licheniformis,* and *B. coagulans* strains that produce various antibiotics with antifungal and antibacterial activity. *B. pumilus* produced bacilysin and iturin A. Bacilysin is a very small compound with a molecular weight of 270 that inhibits only yeast. The iturins, which are soluble in polar solvents, have broad antifungal and antibacterial activity.

In U.S. Pat. No. 5,344,647, Rossall discloses *Bacillus subtilis* strains with broad anti-fungal activity. Additionally, U.S. Pat. No. 5,061,495 to Rossall, provides a novel antibiotic from *B. subtilis* that is 63,500 daltons, precipitates at a pH below 5 and has activity against gram positive bacteria and fungi (Botrytis and Erysiphe). Sholberg et al. (1995) *Can. J. Microbiol.* 41:247–252, Swinburne et al. (1975) *Trans. Brit. Mycol. Soc.* 65:211–217, Singh and Deverall, (1984) *Trans. Br. Mycol. Soc.* 83:487–490, Ferreira et al. (1991) *Phytopathology* 81:283–287 and Baker et al. (1983) *Phytopathology* 73:1148–1152. All disclose the use of Bacillus spp. and *Bacillus subtilis* as biocontrol agents of fungal plant pathogens. Pusey et al. (1988) *Plant Dis.* 72:622–626, Pusey et al., U.S. Pat. No. 5,047,239, and McKeen et al. (1986) *Phytopathology* 76:136–139 disclose control of post harvest fruit rot using *B. subtilis.* McKeen et al., supra, have shown that antibiotics similar to the low molecular weight iturin cyclic polypeptides contribute to this fungicidal activity of *B. subtilis.*

Liu et al., in U.S. Pat. No. 5,403,583 disclose a Bacillus sp., (ATCC 55000) and a method to control the fungal plant pathogen, *Rhizoctonia solani.* Islam and Nandi (1985) *J. Plant Dis. Protect.* 92(3):241–246, disclose a Bacillus sp. with antagonism to *Drechslera oryzae*, the causal agent of rice brown spot. The same authors, Islam and Nandi (1985) *J. Plant Dis. Protect.* 92(3):233–240, also disclose in-vitro antagonism of Bacillus sp. against *Drechslera oryzae, Alternaria alternata* and *Fusarium roseum.* They discuss three components in the culture filtrate. The most active antibiotic was highly soluble in water and methanol with a UV peak at 255 nm and a shoulder at 260 nm that proved to be a polyoxin-like lipopeptide. Cook et al. (1987) *Beltwide Cotton Production Research Conferences*, Dallas, Tex., pp. 43–45, disclose the use of a suspension of Bacillus sp. to reduce the number of cotton plants killed by *Phymatotrichum omnivorum*, a cause of cotton root rot.

B'Chir and Namouchi (1988) *Revue Nématologique* 11(2):263–266, report on a *Bacillus pumilus* that stimulates nematode trapping fungi to increase their ability to trap nematodes. B'Chir and Belkadhi (1986) *Med. Fac. Landbouww. Ryiksuniv. Gent* 51/3b:1295–1310, discuss the cellular interactions of a fungus (Fusarium) and nematodes that cause infection in citrus. The fungus is associated with *B. pumilus* (they occur together) and when the nematode is also there, the fungus is more severe. *B. pumilus* appears to be providing food for the nematodes. Gokte and Swarup (1988) *Indian J. Nematol.* 18(2):313–318, report on *B. pumilus* that are nematicidal, but they do not report any antifungal activity. Slabospitskaya et al. (1992) *Mikrobiol Zh* (*Kiev*) 54(6):16–22, compare many different Bacillus, including *B. pumilus* for their ability to produce chitinases, but they report no activity on plant pathogens. The *B. pumilus* produce the lowest chitinase levels. McInroy et al. (1995) *Plant and Soil* 173(2):337–342, did a survey of the many types of bacteria, including many Bacillus and *B. pumilus* that are endophytes within plant stems and roots. However, they show no evidence that these endophytic strains are antifungal. Chemin et al. (1995) *Molecular Genetics,* found a *Bacillus pumilus* that has a wide spectrum of activity against bacteria (e.g., Xanthomonas, Pseudomonas, Erwinia) and fungi that cause plant disease. Fey et al. (1991) *Akad Landwirts Kart,* report on *B. pumilus* strains that provide seed potatoes some protection from *Rhizoctonia solani.*

DISCLOSURE OF THE INVENTION

A novel antibiotic-producing Bacillus sp. is provided that exhibits antifungal activity only on certain specific plant pathogens and no antibacterial activity. Also provided is a method of treating or protecting plants, fruit and roots from fungal infections comprising the step of applying an effective amount of an antibiotic-producing Bacillus sp. The antibiotic-producing Bacillus sp. can be provided as a suspension in a whole broth culture or as a partially-purified antibiotic-containing supernatant obtained from a whole broth culture of an antibiotic-producing Bacillus sp. Also provided is a novel water-soluble antibiotic that exhibits specific antifungal activity and no antibacterial activity.

The present invention also provides a novel compound that enhances the insecticidal activity of *B. thuringiensis.* The compound is isolated from whole broth culture or supernatant of *B. pumilus,* that when combined with *B. thuringiensis,* enhances its insecticidal activity. The invention also includes methods of treating plants to control insect infestations on or in plants with a bacterial suspension of a Bacillus or a metabolite-containing supernatant of a culture of a Bacillus or purified metabolites.

The present invention further provides combining strain B-30087 with strain B-21661 (AQ 713) for use as fungicides, where the use of the strains together provides a greater efficacy than if either were used alone.

BRIEF DESCRIPTION OF THE DRAWINGS

FIG. 1 is an NMR spectrum recorded at 400 MHz in $D_2O$, of a partially-purified fungicidal fraction of Bacillus sp. deposited under NRRL Accession No. B-30087.

FIG. 2 shows the $^1H$ NMR spectrum of zwittermicin A recorded at 400 MHz in $D_2O$.

FIGS. 3A through 3C are capillary electropherograms of supernatant isolated from Bacillus as described in Example 9. Conditions for the electrophoresis: an uncoated 56 cm capillary was used at 40C, 30 kV, positive polarity, 100 µA with pH5.8 sodium phosphate buffer, UV detection at 200 nm.

FIG. 4 compares three electropherograms from a capillary electrophoresis (CE) analysis of a partially-purified fraction of NRRL Accession No. B-30087 alone (FIG. 4A), a partially-purified fraction of NRRL No. B-30087 with zwittermicin A (FIG. 4B), and zwittermicin A alone (FIG. 4C).

MODES FOR CARRYING OUT THE INVENTION

The present invention provides a biologically pure culture of a strain having all the identifying characteristics of a novel strain of Bacillus sp. and mutants or variants thereof, with antifungal activity only on specific plant pathogens such as rusts, powdery mildews and downy mildews. This novel strain of *B. pumilus* was deposited on Jan. 14, 1999, with the Agricultural Research Culture Collection (NRRL), 1815 North University Street, Peoria, Ill. 61604, USA, and accorded Accession No. NRRL B-30087, under the provisions of the Budapest Treaty on the International Recognition of the Deposit of Microorganisms for the Purpose of Patent Procedure. The strain designated NRRL B-21661 was deposited with the same institution on Mar. 7, 1997. It was subsequently identified as *Bacillus subtilis* by the American Type Culture Collection (ATCC).

The invention also includes methods of preventing and treating fungal diseases in plants, including plant roots, using such bacterial strains or antibiotic-containing supernatants or pure antibiotics obtained from such bacterial strains. The invention also includes a water-soluble antifungal antibiotic with a molecular weight of less than 10,000 daltons, slightly heat labile, positively charged, and an HPLC peak with UV absorbance at a maximum of 280 nm and a shoulder at 230 nm. The antibiotic is not zwittermicin A.

Further aspects of the invention include a whole broth culture or supernatant of *B. pumilus* that when combined with *B. thuringiensis* enhances the insecticidal activity of *B. thuringiensis*. The invention also includes methods of treating plants to control insect infestations on or in plants with a bacterial suspension of a Bacillus or a metabolite-containing supernatant of a culture of a Bacillus or purified metabolites.

A further aspect of the invention is unexpected synergistic effect of using the combination of a strain of *B. pumilus* (NRRL B-30087) with *B. subtilis* (NRRL B-21661) as a fungicide. The invention includes the compositions and methods of using them as fungicides.

Definitions

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The term "isolated" is used interchangeably with "biologically pure" and means separated from constituents, cellular and otherwise, in which the strain or metabolite is normally associated with in nature.

As used herein, "biological control" is defined as control of a pathogen or insect by the use of a second organism. Known mechanisms of biological control include enteric bacteria that control root rot by out-competing fungi for space on the surface of the root. Bacterial toxins, such as antibiotics, have been used to control pathogens. The toxin can be isolated and applied directly to the plant or the bacterial species may be administered so it produces the toxin in situ.

The term "fungus" or "fumgi" includes a wide variety of nucleated spore-bearing organisms that are devoid of chlorophyll. Examples of fungi include yeast, molds, mildews, rusts, and mushrooms.

The term "bacteria" includes any prokaryotic organism that does not have a distinct nucleus.

"Fungicidal" means the ability of a substance to increase mortality or inhibit the growth rate of fungi.

"Antibiotic" includes any substance that is able to kill or inhibit a microorganism. Antibiotics may be produced by a microorganism or by a synthetic process or semi-synthetic process. The term, therefore, includes a substance that inhibits or kills ftmgi for example, zwittermicin A or kanosamine.

"Antifungal" includes any substance that is able to kill or inhibit the growth of fungi.

The term "culturing" refers to the propagation of organisms on or in media of various kinds.

"Whole broth culture" refers to a liquid culture containing both cells and media. "Supernatant" refers to the liquid broth remaining when cells grown in broth are removed by centrifugation, filtration, sedimentation, or other means well known in the art.

As used herein, the term "insects" includes all organisms in the class "Insecta." "Pre-adult" insects refers to any form of an organism prior to the adult stage, including, for example, eggs, larvae, and nymphs. "Insecticidal" refers to the ability of a substance to increase mortality or inhibit growth rate of insects. "Nematicidal" refers to the ability of a substance to increase mortality or inhibit the growth rate of nematodes. "Pesticidal" refers to the ability of a substance to increase mortality or inhibit the growth rate of insects, nematodes and mites.

"Positive control" means a compound known to have pesticidal activity. "Positive controls" include, but are not limited to, commercially available chemical pesticides. The term "negative control" means a compound known not to have pesticidal activity. Examples of negative controls are water or ethyl acetate.

The term "solvent" includes any liquid that holds another substance in solution. "Solvent extractable" refers to any compound that dissolves in a solvent and which then may be isolated from the solvent. Examples of solvents include, but are not limited to, organic solvents like ethyl acetate.

The term "metabolite" refers to any compound, substance or byproduct of a fermentation of a microorganism that has pesticidal activity. Antibiotic as defined above is a metabolite specifically active against a microorganism.

A "composition" is intended to mean a combination of active agent and another compound or composition, inert (for example, a detectable agent or label) or active, such as an adjuvant.

A "fraction" is intended to mean an aliquot from a fractionation assay used to separate the molecules of the supernatant by size, polarity or charge.

A "partially-purified fraction" is one of the aliquots collected in the fractionation assay that is able to inhibit germination in a bioassay or enhance B+activity against lepioloplaus.

An "effective amount" is an amount sufficient to effect beneficial or desired results. An effective amount can be applied in one or more applications. In terms of treatment and protection, an "effective amount" is an amount sufficient to ameliorate, stabilize, reverse, slow or delay progression of insect infestation.

We describe a biologically pure culture of a strain having all the identifying characteristics of a novel antibiotic-producing strain of Bacillus sp. deposited under NRRL Accession No. B-30087, and mutants thereof, that have antifungal activity only on specific plant pathogens and no antibacterial activity. In one aspect, the strain is *Bacillus pumilus* deposited under NRRL Accession No. B-30087, and mutants of the strain.

In other aspects, the strain is a mutant or variant of NRRL Accession No. B-30087 that has all the identifying characteristics (as provided below) of the strain deposited under NRRL Accession No. B-30087. Mutant or variant are used interchangeably throughout this disclosure and further, may be identified as having a genome that hybridizes under conditions of high stringency to the genome of NRRL Accession No. B-30087. "Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. Hybridization reactions can be performed under conditions of different "stringency." In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

A mutant or variant of NRRL Accession No. B-30087 may also be defined as a strain having a genomic sequence that is greater than 85%, more preferably greater than 90% or more preferably greater than 95% sequence identity to the genome of NRRL Accession No. B-30087. A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example, those described in *Current Protocols in Molecular Biology* (F. M. Ausubel et al., eds., 1987) Supplement 30, section 7.7.18, Table 7.7.1. Preferably, default parameters are used for alignment. A preferred alignment program is. BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/cii-bin/BLAST.

This invention further provides the supernatants obtained from the above noted cultures. The supernatant may be obtained by methods well known in the art including: centrifugation; filtration; sedimentation; and the like.

In another aspect, the invention encompasses an isolated metabolite that is a water-soluble antifuingal antibiotic. The metabolite is isolated from the strains of this invention and described above. It has the chemical characteristics of being less than 10,000 daltons, UV absorption peak at 280 nm and shoulder at 230 nm, acid and base stable, slightly heat labile over 80° C., and positively charged with activity on specific plant pathogens, but with no activity on bacteria. This invention further provides a process for producing this metabolite, the method comprising culturing a strain of this invention and isolating the active metabolite using the methods described below.

A flurther aspect of the invention is a partially-purified active fraction of NRRL Accession No. B-30087 that has fungicidal activity. The active fraction is not identical to zwitternicin A.

Further provided by this invention are compositions comprising any of the above strains (including mutants or variants thereof), supernatants, fractions and metabolites, alone or in combination with each other, and a carrier. These compositions may be further supplemented by the addition of at least one chemical or biological pesticide. These compositions may take the form of various formulations, which include, but are not limited to, a wettable powder, a granule formulation, an aqueous suspension, an emulsifiable concentrate or microencapsulation.

In order to achieve good dispersion and adhesion of compositions within the present invention, it may be advantageous to formulate the whole broth culture, supernatant, fraction and/or metabolite/antibiotic with components that aid dispersion and adhesion. Accordingly, suitable formulations will be known to those skilled in the art (wettable powders, granules and the like, or can be microencapsulated in a suitable medium and the like, liquids such as aqueous flowables and aqueous suspensions, and emulsifiable concentrates). Other suitable formulations will be known to those skilled in the art.

Any of the above noted strains, metabolites, fractions, supernatants and compositions containing these active ingredients, may be used to provide a method of treating or protecting plants, roots or fruit from fungal infections. The method comprises applying an effective amount of a strain, metabolite, fraction, supernatant or compositions containing these active ingredients, alone or in combination with each other and/or another biologic or chemical pesticide, to the infected root, plant or fruit. Effective amounts of these compositions also can be applied to a plant, root or fruit to prevent such infestation.

In a further aspect, the invention encompasses a method of treating or protecting plants, roots or fruit from fungal diseases comprising applying an effective amount of the antibiotic produced by a strain, or variant thereof, having all the identifying characteristics of the novel strain Bacillus sp. NRRL Accession No. B-30087. In one embodiment, the strain is Bacillus sp. NRRL Accession No. B-30087.

This invention further provides a water-soluble compound that enhances the insecticidal activity of *Bacillus thuringiensis*, wherein the compound has the molecular weight of less than 10,000 daltons and the compound is not zwittermicin A. The compound is not beta exotoxin or other *Bacillus thuringiensis*-produced exotoxin.

The compound is isolated by anion exchange resin, acetonitrile precipitation and size exclusion chromatography (SEC). This invention also provides a partially purified fraction of the supernatant of a Bacillus that contains the novel compound. The novel compound and active fraction can be isolated from a Bacillus selected from the group of Bacillus spp., including but not limited to *B. subtilis, B. cereus, B. mycoides*, and *B. pumilus*.

The partially purified active fraction can be identified by its $^1$HNMR (or proton NMR) spectrum which allows a chemist skilled in the art to determine if a compound has been fully purified. When a compound is pure, a peak representing one proton will integrate for an arbitrary value of one. Peaks representing two protons, for example a methylene group, will then integrate for a value of two. Peaks representing three protons, for example a methyl group, will then integrate for three. This is the case for FIG. 3, pure zwittermicin A standard. However, the $^1$H NMR spectrum of the active partially purified *Bacillus thuringiensis* enhancer has a group of peaks that integrate for less than one and therefore belong to a separate compound from the larger peaks in the spectrum.

In isolation, the compound does not exhibit insecticidal activity. Combination with *Bacillus thuringiensis* enhances the insecticidal effect of *Bacillus thuringiensis* when applied to plants and plant roots. *Bacillus thuringiensis* can be in the form of a microbial strain, a commercial product, an engineered plant, an insecticidally active metabolite, an insecticidally active supernatant or a delta endotoxin.

*Bacillus thuringiensis* is a Gram-positive, spore-forming bacterium characterized by parasporal crystalline protein inclusions. The proteins can be highly toxic to pests and specific in their toxic activity. As used in the claims below, the term "*Bacillus thuringiensis*" includes microbial strains, commercial products containing such strains or isolates containing active metabolites or fractions isolated from the strains, genetically modified or engineered plants that express a gene encoding *Bacillus thuringiensis* insecticidal protein or gene product or a delta endotoxin. Toxin genes have been isolated and sequenced, and recombinant DNA-based *Bacillus thuringiensis* products have been produced and approved for use. Genetic engineering techniques and new approaches for delivering these *Bacillus thuringiensis* endotoxins to agricultural environments are under development and commercial production. This includes the use of plants genetically engineered with endotoxin genes for pest resistance and the use of stabilized intact microbial cells as *Bacillus thuringiensis* endotoxin delivery vehicles (Gaertner, et al. (1988) TIBTECH 6:S4–S7). *Bacillus thuringiensis* can be made available to the target pest by exposing the target pest to wild-type *Bacillus thuringiensis* which naturally express the toxin. Alternatively, a gene encoding a desired toxin can be transformed into and expressed in a suitable recombinant host. Fragments of the *Bacillus thuringiensis* toxins that retain insecticidal activity can also be used.

The following United States Patents disclose pesticidal *Bacillus thuringiensis* isolates or recombinant microbes which express a *Bacillus thuringiensis* toxin: U.S. Pat. Nos. 5,006,335; 5,106,620; 5,045,469; 5,135,867; 4,990,332; 5,164,180; 5,126,133; 5,093,119; 5,208,017; 5,186,934; 5,185,148; 5,211,946; 4,948,734; 4,849,217; 4,996,155; 4,999,192; 4,966,765; 5,073,632; 5,196,342; 5,063,055; 5,080,897; 5,024,837; 5,147,640; 5,173,409; and 5,186,934.

Preparations of the spores and crystals of *Bacillus thuringiensis* subsp. kurstaki have been used for many years as commercial insecticides for lepidopteran pests. For example, *Bacillus thuringiensis* var. kurstaki HD-1 produces a crystal called a -delta endotoxin which is toxic to the larvae of a number of lepidopteran insects. Additional species of *Bacillus thuringiensis* namely israelensis and tenebrionis have been used commercially to control insects The cloning and expression of a *Bacillus thuringiensis* crystal protein gene in *Escherichia coli* has been described in Schnepf, H. et al. (1981) *Proc. Natl. Acad. Sci. USA* 78:2893–2897. U.S. Pat. No. 4,448,885 and U.S. Pat. No. 4,467,036 both disclose the expression of a crystal protein in *E. coli*. Hybrid *Bacillus thuringiensis* crystal protein genes have been constructed that exhibit increased toxicity and display an expanded host range to a target pest. See, U.S. Pat. Nos. 5,128,130 and 5,055,294. U.S. Pat. Nos. 4,797,276 and 4,853,331 disclose *Bacillus thuringiensis* strain San Diego (a.k.a. *B.t. tenebrionis*, a.k.a. M-7) which can be used to control coleopteran pests in various environments. U.S. Pat. No. 4,918,006 discloses *Bacillus thuringiensis* having activity against dipterans. U.S. Pat. No. 4,849,217 discloses *Bacillus thuringiensis* isolates that have activity against the alfalfa weevil. U.S. Pat. No. 5,151,363 and U.S. Pat. No. 4,948,734 disclose certain isolates of *Bacillus thuringiensis* which have activity against nematodes.

*Bacillus thuringiensis* cultures also are available from the United States Department of Agriculture (USDA) in Brownsville, Tex. Requests should be made to USDA, ARS, Cotton Insects Research Unit, P.O. Box 1033, Brownsville, Tex. 78520 USA; or at the Northern Research Laboratory, U.S. Department of Agriculture, 1815 North University Street, Peoria, Ill., USA.

Therefore, the compound and the active fraction enhance the insecticidal activity of *Bacillus thuringiensis* against insects, which include but are not limited to nematodes, flies, armnyworm, mites, Colorado potato beetle and corn rootworm.

As is well known to those of skill in the art, the active compound can be applied in the form of a composition. Accordingly, this invention also provides a composition comprising the novel compound and a carrier, such as a solvent or agriculturally suitable carrier. In a further embodiment, the composition further includes an effective amount *Bacillus thuringiensis*, as described above. In a yet further embodiment, the composition includes at least one chemical or biological pesticide as is conventionally used in the art. In order to achieve good dispersion and adhesion of compositions within the present invention, it may be advantageous to formulate the whole broth culture, supernatant and/or metabolite with components that aid dispersion and adhesion. For ease of application to plants or plant roots, the formulations can be processed into a formulation selected from the group consisting of a wettable powder, an aqueous suspension, an emulsifiable concentrate and a microencapsulated formulation.

The novel compound, active fraction or compositions containing them can be used to enhance the insecticidal activity of Bacillus thuringiensis. Thus, this invention also provides a method to enhance the insecticidal activity of Bacillus thuringeinsis by combining an effective enhancing amount of the novel compound, active fraction or composition containing them with Bacillus thuringiensis. In a further aspect, an effective amount of at least one biopesticide or chemical pesticide is added to the formulation.

The invention further comprises using the novel compound, NRRL Accession No. B-30087 in combination with NRRL Accession No. B-21661, applied as whole broth culture on a plant, root or fruit, for use as a ftimgicide, said fungicide having a more potent effect as a result of the unexpected synergistic effect of the combination of compounds. More preferably, the combination is applied in a ratio of 1:2 (B-21661:B-30087) to Botrytis cinerea or Peronospora parasitica. Even more preferably, the combination is applied to Botrytis cinerea or Peronospora parasitica in a 1:4 ratio. In a yet further embodiment, the composition includes at least one chemical or biological pesticide as is conventionally used in the art. In order to achieve good dispersion and adhesion of compositions within the present invention, it may be advantageous to formulate the whole broth culture, supematant and/or metabolite with components that aid dispersion and adhesion. For ease of application to plants or plant roots, the formulations can be processed into a formulation selected from the group consisting of a wettable powder, an aqueous suspension, an emulsifiable concentrate and a microencapsulated formulation.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

EXAMPLES

The following examples are intended to illustrate, but not limit the invention.

Example 1

Characterization of Strain NRRL Accession No. B-30087.

NRRL Accession No. B-30087 was identified based on whole-cell cellular fatty acids, derivatized to methyl esters - FAMEs (Miller, L. T. (1982) "Single derivatization method for routine analysis of bacterial whole cell wall fatty acid methyl esters, including hydroxy acids" *J. Clin. Microbiol.* 16:584–586) and analyzed by gas chromatography using the MIDI system (Microbial Identification System, Inc., Newark, Del.). The procedure and protocols used for growing the bacterial cultures and instrument specifications are described by MIDI (identification of bacteria by gas chromatography of cellular fatty acids. Technical Note #101. MIDI, Inc., 115 Barksdale Professional Center, Newark, Del.). Isolates were grown on TSA (BBL) plates at 28° C. for 24 hours and cells harvested. One ml of a methanolic NaOH (15% [wt/vol] NaOH in 50% [vol/vol] methanol) was added and cells were saponified at 100° C. for 30 minutes. Esterification of fatty acids was performed with 2 mls of 3.25 N HCl in 46% (vol/vol) methanol at 80° C. for 10 minutes. The FAMEs were extracted into 1.25 ml of 1:1 (vol/vol) methyl-tert-butyl ether-hexane, and the organic extract washed with 3 ml of 1.2% (wt/vol) NaOH before analysis by gas chromatography. The gas chromatograph (Hewlett-Packard 5890A) was equipped with a flame ionization detector and capillary column (Hewlett-Packard 19091 B- 102, Cross-linked 5% phenyl-methyl silicone; 25 m×0.22 mm ID; film thickness, 0.33 11 m; phase ratio of 150) with hydrogen as the carrier gas. A Hewlett-Packard 3392 integrator automatically integrated FAME peaks and bacterial isolates named using the MIDI Microbial Identification Software (Sherlock TSBA Library version 3.80). The FAME profile of *Xanthomonas maltophila* ATCC 13637 was used as reference check for the MIDI determinations.

The results of the three separate runs of the MIDI profile identified NRRL Accession No. B-30087 as a *Bacillus pumilus* with a similarity index score of 0.875.

Example 2

Activity of NRRL Accession No. B-30087 Against Plant Pathogens in in Vitro Culture (Zone Assay).

To determine if NRRL Accession No. B-30087 is effective against a wide range of plant pathogenic fungi, the following experiment was performed using these plant pathogens: *Botrytis cinerea, Alternaria brassicicola Colletotrichum acutatum, Cladosporium carophylum, Moniliniafructicola, Venturia inaequalis, Rhizoctonia solani, Sclerotinia sclerotiorum, Fusarium oxysporum, Taphrina deformans,* and *Verticillium dahliae.*

To determine the activity of NRRL Accession No. B-30087 in an agar diffusion (zone) assay, plant pathogen spores (spores were scraped from the surface of petri plates and diluted to approximately $1 \times 10^5$ spores/ml (depending on the pathogen)) were spread over the surface of potato dextrose agar in 10 cm petri dishes. For *Rhizoctonia solani* and *Sclerotinia sclerotiorum*, mycelial fragments instead of spores were spread onto the plates. Circular wells, approximately 7.0 mm were removed from the agar and a 125 1 sample of the supernatant of NRRL Accession No. B-30087 grown in a soy, yeast extract medium in 250 ml shake flasks for 72 hours was placed in the well.

Supernatant was prepared by centrifuging at 12,000 rpm for 10 minutes. Typical results can consist of a zone of no growth and/or reduced growth of the pathogen around the well or no zone at all. The zone size in millimeters was measured and recorded if there was a zone. The results are shown in Table 1, below.

TABLE 1

In vitro test of NRRL Accession No. B-30087 against fungal plant pathogens

| | |
|---|---|
| Alternaria brassicicola | No Zone |
| Botrytis cinerea | No Zone |
| Cladosporium carpohilum | No Zone |
| Colletotrichum acutatum | No Zone |
| Fusarium oxysporum | No Zone |
| Monilinia fructicola | No Zone |
| Rhizoctonia solani | No Zone |
| Sclerotinia sclerotiorum | No Zone |
| Taphrina deformans | No Zone |
| Venturia inaequalis | No Zone |
| Verticillium dahliae | No Zone |
| Pythium sp. | No Zone |

TABLE 1-continued

In vitro test of NRRL Accession No. B-30087 against fungal plant pathogens

| | |
|---|---|
| Phytophthora infestans | Weak activity (small, hazy zone) |
| Phytophthora capsici | No Zone |
| Didimella bryonia | No Zone |

NRRL Accession No. B-30087 supernatant showed no activity against most fungal plant pathogens in zone tests.

Example 3
Activity of NRRL Accession No. B-30087 Against Bacterial Plant Pathogens.

A standard agar diffusion assay was set up as in Example 2. A lawn of each bacterial pathogen was spread over the surface of potato dextrose agar. A 125 l sample of NRRL Accession No. B-30087 supernatant was placed in each well as described previously. The presence of a zone or size of the zone was measured in millimeters.

TABLE 2

In vitro Inhibition of Bacterial Plant Pathogens (Zone Test)

| NRRL No. B-30087 Supernatant: | Inhibition Zone (mm) |
|---|---|
| Pseudomonas syringae pv. Tomato | No Zone |
| Xanthomonacampestris pv. Campestris | No Zone |
| Erwinia carotovora subsp. Carotovora | No Zone |

NRRL Accession No. B-30087 was not active against any species of bacterial plant pathogens tested in vitro.

Example 4
Activity of NRRL Accession No. B-30087 Against Plant Pathogens in Plant Tests.

The activity of NRRL Accession No. B-30087 was tested against bean rust, *Uromyces phaseoli* on snap bean, and gray mold, *Botrytis cinerea* on pepper plants, *Alternaria solani* on tomato plants, and downy mildew of lettuce, *Bremia lactucae*; downy mildew of Brassica, *Peronospora parasitica*, late blight of tomato, *Phytophthora infestans*, and grape powdery mildew, *Uncinula necator*.

*Alternaria solani*

The pathogen, *Alternaria solani*, was grown on standard petri plate (10 cm) with PDA. Fungal colonies are cut from the plate and placed on sporulation medium (20 g sucrose, 30 g calcium carbonate, and 20 g agar per liter of sterile water). Sterile water is added to the plate to partially cover the mycelial blocks and plates are incubated at 22–26° C. with a 14 hour photoperiod for two days. Spores are harvested by scraping the mycelial blocks into a beaker of sterile water. The spore suspension is adjusted to $2 \times 10^4$ spores/ml).

Tomato seedlings (UC82-B) at the 3–4 leaf stage planted in two inch pots and placed in flats, were sprayed with an artists air brush to runoff with NRRL Accession No. B-30087 whole broth grown in a soy flour, yeast extract medium for 72 hours in 250 ml shake flasks. After spraying, the seedlings were allowed to dry a minimum of two hours. Inoculated seedlings were placed in a Percival dew chamber at 22° C. with no illumination for the first 40 hours. The plants in each flat were covered with a plastic dome and kept at 20–22° C. for 48 hours in the Percival incubator at a 14 hour photoperiod. Water without NRRL Accession No. B-30087, with and without spores of the pathogen was used as a negative control and a positive pathogen control. Also, a chemical fungicide (e.g., Azoxystrobin, Abound®) was used for comparison at rates from 100 to 250 ppm. The plants were scored on a scale from 0 to 5, where 5 is 100% infected and 0 has no symptoms present. On the water *A. solani* control, there were uniform lesions over all the leaves and the cotyledons were detached and severely infected (rating of 5=complete infection, no control). NRRL Accession No. B-30087 treated plants looked no different from the water control. There was no control of the pathogen by NRRL Accession No. B-30087 (also a rating of 5). The negative control was not infected. The chemically treated plants had a score between 0 and 1.

*Botrytis cinerea*

The pathogen, *Botrytis cinerea*, was grown on standard petri plate (10 cm) with PDA and spores were collected using potato dextrose broth (PDB) supplemented with malt (0.5 g/L) and yeast extract (0.5 g/L) and adjusted to $1 \times 10^6$ spores/ml. The plants used were peppers (Yolo Wonder) grown in two inch pots to the 3–5 true leaf stage. The application of NRRL Accession No. B-30087 and the pathogen were the same as above. Flats with pots were incubated at a constant 20° C. with no illumination. They were covered with plastic domes and left for 2.5 days (60 to 65 hours) until scoring.

A chemical fungicide (e.g., Iprodione, Rovral®) was used for comparison at rates from 20 to 100 ppm. The plants were scored on a scale from 0 to 5, where 5 is 100% infected and 0 has no symptoms present. On the water *B. cinerea* control, there were uniform lesions over all the leaves (rating of 5=complete infection, no control). NRRL Accession No. B-30087 treated plants looked no different from the water control. There was no control of the pathogen by NRRL Accession No. B-30087 (also a rating of 5). The negative control was not infected. The chemically treated plants had a score between 0 and 1.

*Bremia lactucae*

For the Bremia test, lettuce seeds were planted in a layer of sterilized potting mix containing peat, perlite and vermiculite in small clear plastic plant boxes measuring about 8 centimeters high and square. One week after planting, the lettuce seedlings were sprayed with the NRRL Accession No. B-30087 broth or supernatant sample. The plants were allowed to dry and then a downy mildew spore suspension collected from infected lettuce seedlings ($2 \times 10^4$ spores/ml) was sprayed onto the seedlings. Chemical standards consisting of Aliette (fosetyl-al) and Ridomil (metalaxyl) were also applied. However, the isolate of *Bremia lactucae* used in these tests was previously demonstrated to be insensitive to these two chemical standards that are used commercially. The plastic boxes were covered with tight fitting lids and incubated at 15–16° C. in a Percival incubator for 16 hours without illumination. Plastic boxes were then placed at room temperature (20–26° C.) under lights for six days. Seedlings were uncovered, sprayed with water, recovered, and returned to the incubator at 15–16° C. for sporulation to occur overnight. The effect of NRRL Accession No. B-30087 against a chemically-resistant strain of lettuce downy mildew is shown below in Table 3.

TABLE 3

| | Score | | |
|---|---|---|---|
| | Rep 1 | Rep 2 | Rep 3 |
| NRRL No. B-30087 Sample 1 | 0.0 | 1.0 | 1.0 |
| NRRL No. B-30087 Sample 2 | 1.0 | 1.0 | 0.0 |

TABLE 3-continued

|  | Score | | |
|---|---|---|---|
|  | Rep 1 | Rep 2 | Rep 3 |
| Aliette 240 ppm | 5.0 | 3.0 | — |
| Ridomil 125 ppm | 3.0 | 3.0 | — |
| Water check | 5.0 | 5.0 | 5.0 |

NRRL Accession No. B-30087 had excellent activity against lettuce downy mildew with little to none sporulation of the pathogen on the seedlings, whereas the control (water check) plants were completely sporulated with downy mildew. The chemical standards did not effectively control the pathogen.

*Peronospora parasitica*

Bacillus strain NRRL Accession No. B-30087 was grown as above in 250 ml shake flasks. The whole broth culture at 1× strength was sprayed onto one week-old cauliflower or brussel sprout plants at the full cotyledon stage with an artist's air brush powered by compressed air. Three replicates of 15–25 seedlings/pot were sprayed per treatment. A spore suspension of downy mildew, *Peronospora parasitica* at $1–5\times10^4$ spores/ml was sprayed onto the Brassica plants after first applying the NRRL Accession No. B-30087. Chemical standards consisting of Aliette (fosetyl-al) and Ridomil (metalaxyl) were also applied. However, the isolate of *Peronospora parasitica* used in these tests was previously demonstrated to be insensitive to these two chemical standards that are used commercially.

The plants were held at 15–17° C. for 16 hours for infection, then the seedlings were incubated at 20–24° C. for six days. The pots were returned to 15–17° C. overnight for sporulation of the pathogen to occur. Each plant was evaluated by estimating the percent disease control based on a scale from 0 to 5. A zero rating is a plant with no sporulating lesions. The results averaged across replicate pots are shown below in Table 4.

TABLE 4

| | Score | | |
|---|---|---|---|
| | Rep 1 | Rep 2 | Rep 3 |
| NRRL No. B-30087 Sample 1 | 0.5 | 1.0 | 0.5 |
| NRRL No. B-30087 Sample 2 | 0.5 | 0.5 | 1.0 |
| Aliette 240 ppm | 5.0 | 3.0 | — |
| Ridomil 125 ppm | 4.0 | 4.0 | 4.0 |
| Water check | 5.0 | 3.0 | 5.0 |

NRRL Accession No. B-30087 controlled the Brassica downy mildew more effectively as compared to the untreated check and the chemical standards.

*Uncinula necator*

Grape seedlings (Chardonnay) were grown in two inch pots until the 6–9 true leaf stage. The culture of powdery mildew was maintained on grape seedlings at 22–26° C. under a 14 hour photoperiod. All but the youngest 2–4 leaves are removed. The NRRL Accession No. B-30087, the chemical fungicide (Rally®, myclobutanil at 25 ppm) and the water check are applied to runoff as above for the other pathogens tested. Four to five replications are used for each treatment. To inoculate with powdery mildew, leaves with mildew on maintenance seedlings are removed with scissors and each plant is inoculated individually. The surface of the maintenance seedling is gently brushed with a paintbrush so that spores are deposited onto the upper surface of the test plants. The procedure is performed using a 3× lighted magnification lens to assure all plants are getting equivalent inoculum. Flats with pots are placed in the dark for 16–24 hours at 20–24° C. Flats are kept at 22–26° C. with a 14 hour photoperiod for an additional 9–11 days until the test is read. As above, the plants are given a score of 0 to 5. The result using NRRL Accession No. B-30087 is shown below in Table 5.

TABLE 5

| | Score | | | |
|---|---|---|---|---|
| | Rep 1 | Rep 2 | Rep 3 | Rep 4 |
| NRRL No. B-30087 | 0.5 | 0.0 | 1.0 | 1.0 |
| Rally 25 ppm | 0.0 | 0.0 | 0.0 | 0.0 |
| Water check | 5.0 | 5.0 | 3.0 | 4.0 |

NRRL Accession No. B-30087 controlled the Uncinula powdery mildew effectively compared to the untreated check and almost as well as the chemical standard, Rally.

*Phytophthora infestans*

The test of tomato late blight, *P. infestans* was conducted as using tomato seedlings (UC82-B) at the 4–6 true leaf stage grown in two-inch square plastic pots. Applications of NRRL Accession No. B-30087 grown as previously described, were made to the tomato seedlings. Inoculum of *P. infestans* was produced by scraping a sporulating colony grown on rye seed agar and adjusting the inoculum concentration to between 0.7 to $1.0\times10^4$ sporangia/ml. Inoculated seedlings were placed into flats and incubated exactly as described for the *A. solani* test. Seedlings were evaluated on a 0–5 scale. Quadris® (azoxystrobin) was used for comparison at a rate of 62.5 to 125 ppm. The result using NRRL Accession No. B-30087 is shown below in Table 6.

TABLE 6

| | Score | | | | |
|---|---|---|---|---|---|
| | Rep 1 | Rep 2 | Rep 3 | Rep 4 | Rep 5 |
| NRRL No. B-30087 | 2.0 | 1.5 | 1.5 | 0.5 | 2.0 |
| Quadris 125 ppm | 0.0 | 0.0 | 0.0 | 0.0 | 0.0 |
| Quadris 62.5 ppm | 0.0 | 0.5 | 0.0 | 0.5 | 0.0 |
| Water check | 5.0 | 5.0 | 4.0 | 4.0 | 5.0 |

NRRL Accession No. B-30087 controlled late blight nearly as well as the chemical standard, Quadris, after four days of incubation.

*Uromyces phaseoli*

The test of bean rust, *U. phaseoli* was conducted using snap bean seedlings (Provider variety) until the first primary leaves were ¾ expanded. Applications of NRRL Accession No. B-30087 were made as previously described for the other host/pathogen combinations. Inoculum of the rust pathogen was stored as dried rust spores in vials at 20° C. Inoculum was prepared by adding dried rust spores to water with 0.01% Tween 20 and stirred vigorously on a magnetic stirrer for at least one hour. Inoculum is adjusted to $2–4\times10^5$ spores/ml. The primary leaves are inoculated and seedlings are placed in flats and incubated overnight at 20° C. in a Percival dew chamber. Seedlings are then incubated at room temperature (20–26° C.) for an additional 8–10 days. Seedlings are rated on a 0 to 5 scale based on the incidence and severity of sporulating rust pustules present.

The chemical fungicide, Break® (propiconazole) was used for comparison at a rate of 40 ppm. The result using NRRL Accession No. B-30087 whole broth is shown below in Table 7.

TABLE 7

|  | Score | | |
| --- | --- | --- | --- |
|  | Rep 1 | Rep 2 | Rep 3 |
| NRRL No. B-30087 | 0.5 | 0.5 | 0.0 |
| Break ® 40 ppm | 0.0 | 0.0 | 0.5 |
| Water check | 5.0 | 5.0 | 5.0 |

NRRL Accession No. B-30087 controlled bean rust nearly as well as the chemical standard, Break®.

Example 5
Antifungal Metabolite Produced by NRRL Accession No. B-30087.

The whole broth of NRRL Accession No. B-30087 was partitioned into ethyl acetate, butanol and aqueous fractions. Each fraction was tested against snapdragon rust in a spore germination assay. Snapdragon rust spores were germinated in the presence of each sample in a depression microscope slides containing 40 1 of sample and 20 1 of pathogen spores. Approximately 16 hours later the spores are observed under a microscope to see if they have germinated. No germination (score of 0) compared to the water control (100% germination and growth=score of 5) indicates activity of the sample being tested. Results of the rust germination assay with different NRRL Accession No. B-30087 fractions are shown below (score on a 0 to 5 rating as above) in Table 8.

TABLE 8

|  | Score | | |
| --- | --- | --- | --- |
|  | Rep 1 | Rep 2 | Rep 3 |
| Ethyl acetate | 5.0 | 2.0 | 3.0 |
| n-butanol | 3.0 | 5.0 | 3.0 |
| Aqueous | 0.0 | 0.0 | 0.0 |
| Whole broth | 0.0 | 0.0 | 0.0 |
| Water check | 4.0 | 5.0 | 5.0 |

The metabolite is clearly in the water soluble fraction and is not readily extractable in butanol or ethyl acetate.

Other characteristics of the metabolite were determined. The molecule was shown to pass through a 10,000 molecular weight cut off filter indicating the metabolite is smaller than 10,000 daltons. The activity was not lost after treatment with proteases nor when treated with acid or base. The activity was slightly lost upon heating to 80° C. for one hour (the score against snapdragon rust increased from 0 to 1.5). The activity was absorbed on cation resin, but not on anion resin (the metabolite is positively charged).

Exampnle 6
Partial purification of the Fungicidal Fraction of NRRL Accession No. B-30087.

The whole broth culture from NRRL Accession No. B-30087 (850 ml) was centrifuged at 4200 rpm for 15 minutes and the supernatant collected. Activated carbon (30 g) was added to the supernatant and it was shaken well before centrifuging for 20 minutes at 11,500 rpm. The supernatant was dried on a rotary evaporator then redissolved in 15 ml water. The sample was then further purified by size exclusion chromatography (SEC), to separate the components by molecular weight.

P-2 resin (130 g, BioRad) was swelled with milliQ deionized water to pack a column 2.5 cm×80 cm. The 15 ml concentrate was loaded onto the P-2 column, the column eluted with water by gravity and 1 Oml fractions were collected. Parameters for P-2 column: range=2, nm=226 nm,16 mv.

The eluted fractions were assayed using the snapdragon rust germination assay described in Example 5. Fractions 18–24 were found to completely inhibit germination. These fractions were combined and dried on a rotary evaporator, then redissolved in 8 ml water and filtered through 0.2 m filter. This was loaded onto a second P-2 column and run as described above, with the exception that 7 ml fractions were collected.

Fractions 29–38 were found to inhibit germination in the bioassay. These fractions were dried down and then redissolved in water. A small aliquot (Smg) was further separated by HPLC using an amino column (4.6 mm×15 cm, 5 m, 100 angstrom). The column was equilibrated in 0.01 M $KH_2PO_4$ and a gradient was run from 4% to 44% acetonitrile/0.01 M $KH_2PO_4$ for 30 minutes, 1 ml/min detected by UV at 200 nm.

Figure 1:
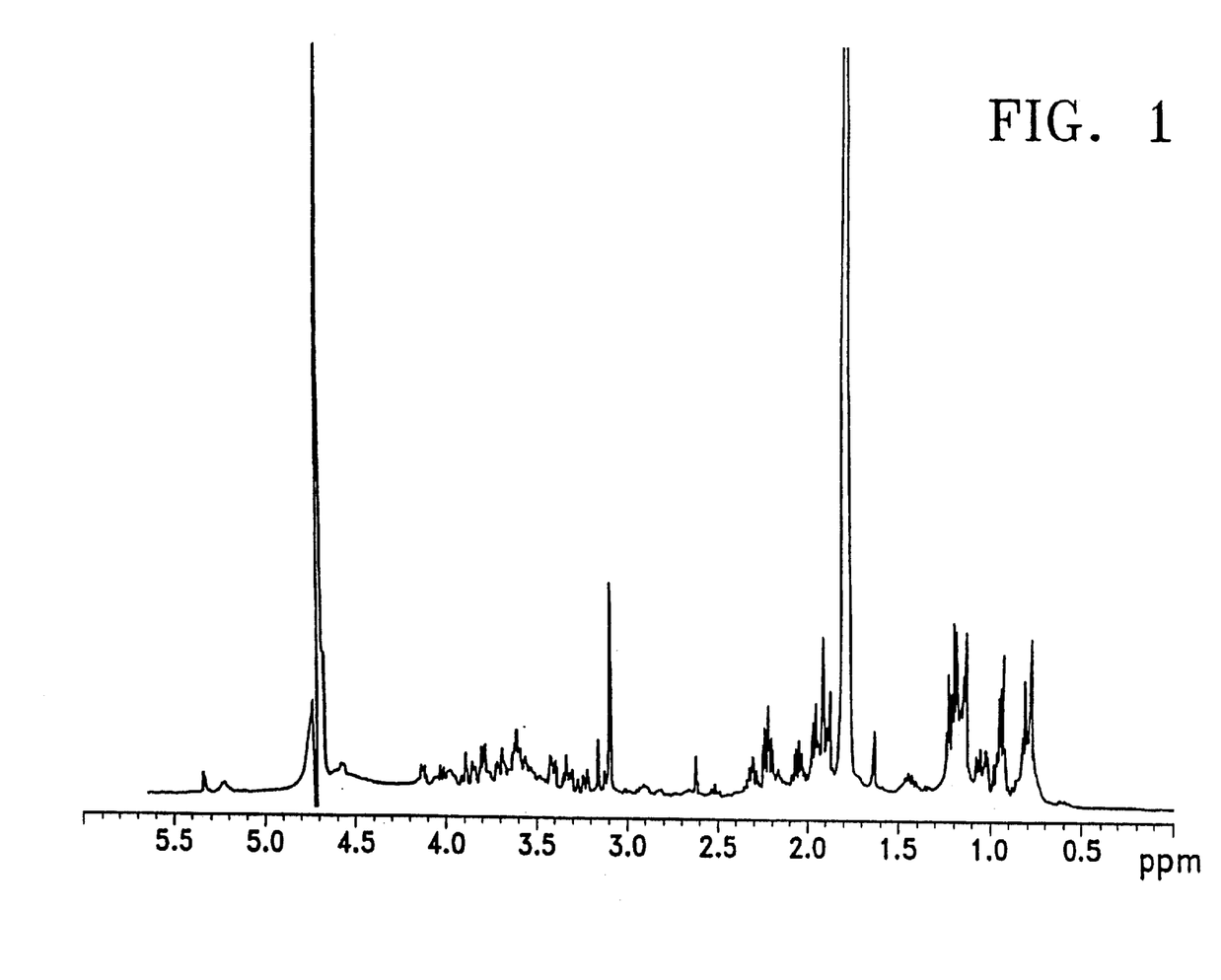

Three peaks were collected and peak 1 was desalted on a size exclusion HPLC column (Toso Haas, G1000 PW, 7.5mm×30 cm, 10 m), eluted with water at 1 ml/min detected by UV at 200 nm. One peak was collected from the size exclusion column and found to be active on the germination assay. A $^1$H-NMR spectrum was recorded at 400 MHz in $D_2O$ of this semi-pure active material as shown in FIG. 1.

Example 7
Chemical Characteristics of the Pungicidal Component are Different than Zwittermicin A.

The fungicidal active fraction of this invention was shown to be different than zwittermicin A on capillary electrophoresis. NRRL Accession No. B-30087 whole broth was grown in a Bacillus culture media containing soy flour, dextrose, yeast extract, $KH_2PO_4$, $K_2HPO_4$, NaCl and $MgSO_4 \times 7H_2O$. Streaked cultures were used to inoculate 250 ml shake flasks. Flasks were shaken at 210 rpm at 30° C. for 4 days.

Figure 3A:
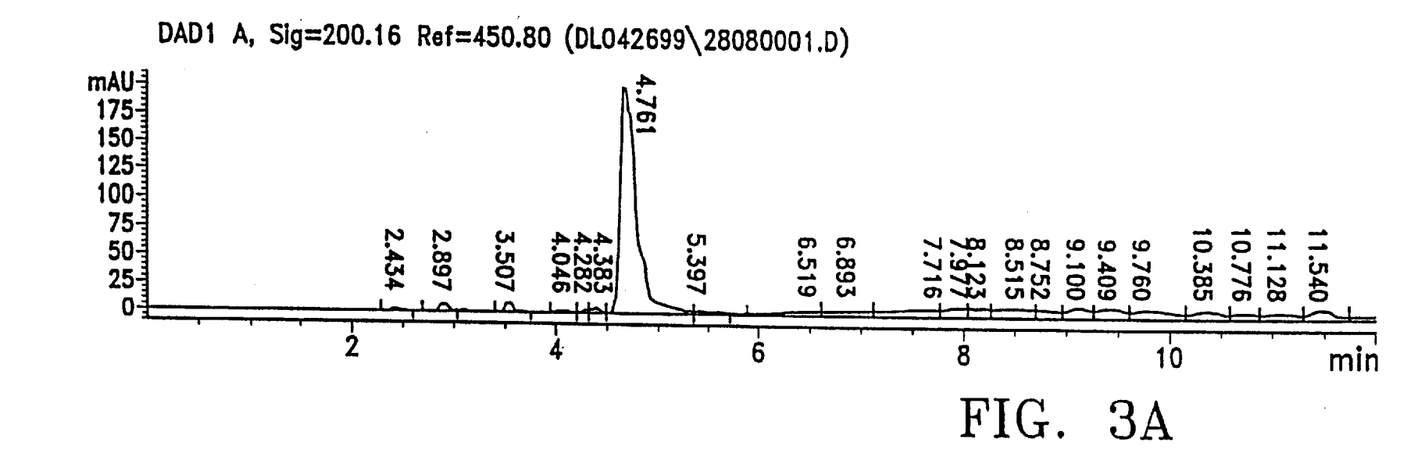
FIG. 3A is the capillary electropherogram of whole broth of *Bacillus pumilus* B-30087.
Figure 3B:
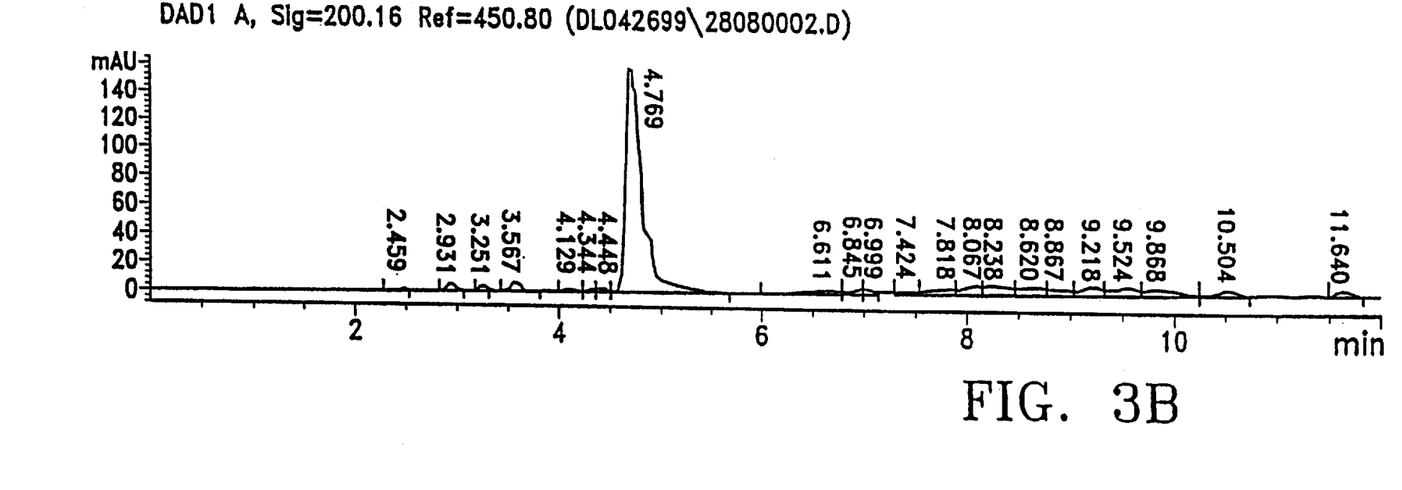
FIG. 3B is the capillary electropherogram of whole broth of *Bacillus pumilus* B-30087 spiked with zwittermicin A standard. The zwittermicin A peak shows up at around a run time of 3.25 minutes; not co-eluting with any peak in the whole broth.
Figure 3C:
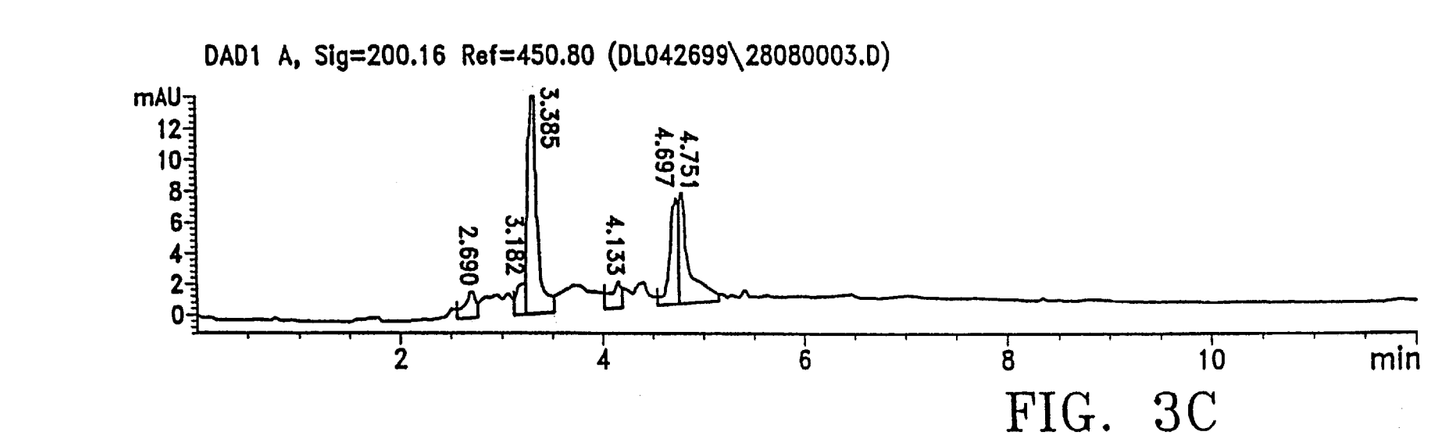
FIG. 3C shows zwittermicin A standard at a run time of about 3.28 minutes.

NRRL Accession No. B-30087 whole broth was spiked with purified zwittermicin A and run on capillary electrophoresis (CE). 30 $\mu l$ of NRRL Accession No. B-30087 whole broth was spiked with 10 $\mu l$ zwittermicin A. One sample each of NRRL Accession No. B-30087 whole broth, NRRL Accession No. B-30087 whole broth with zwittermicin A and zwittermicin A alone, were run on the CE using sodium phosphate buffer at pH 5.8. The generated electropherograms for each sample are shown in FIG. 3.

Figure 2:
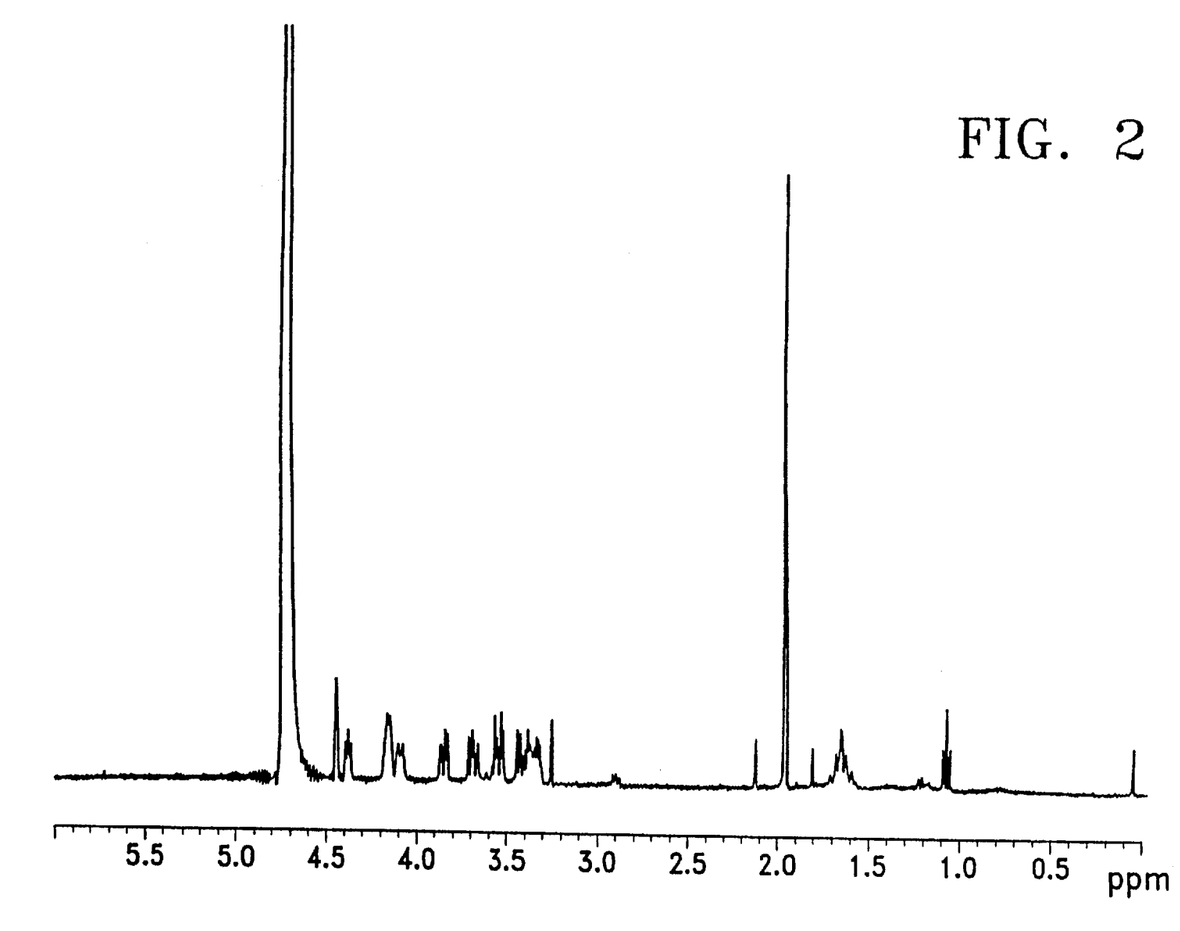
Figure 4A:
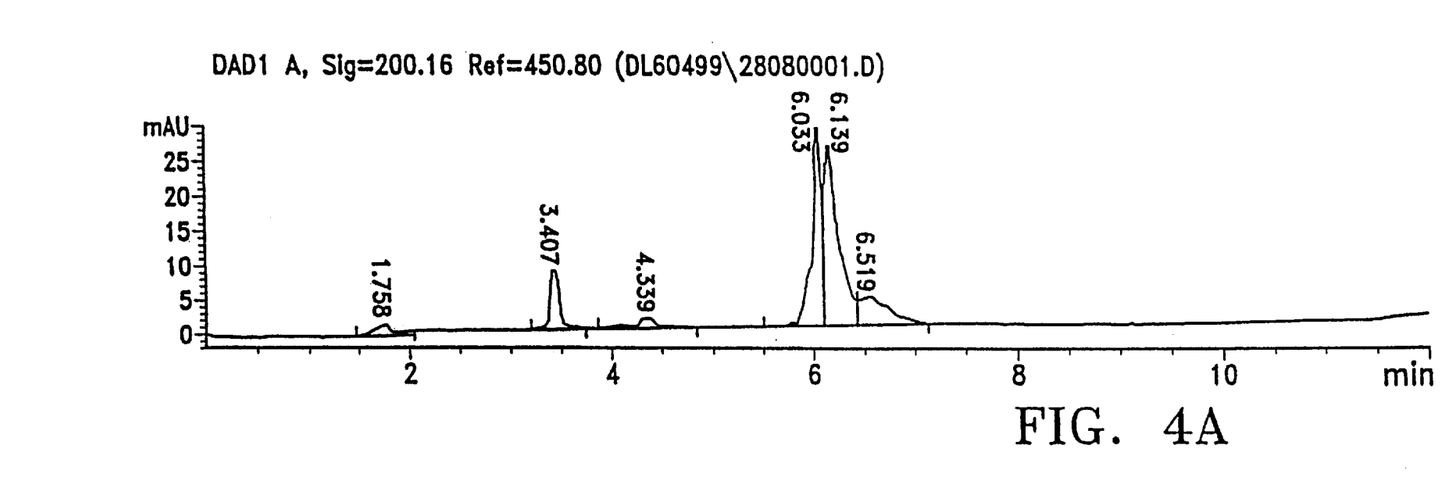
Figure 4B:
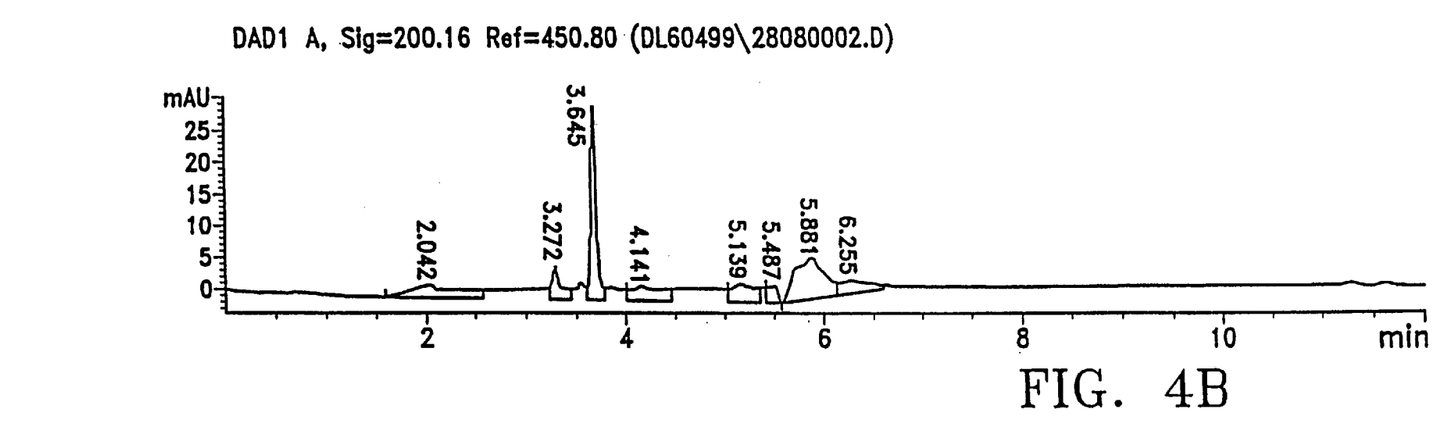
Figure 4C:
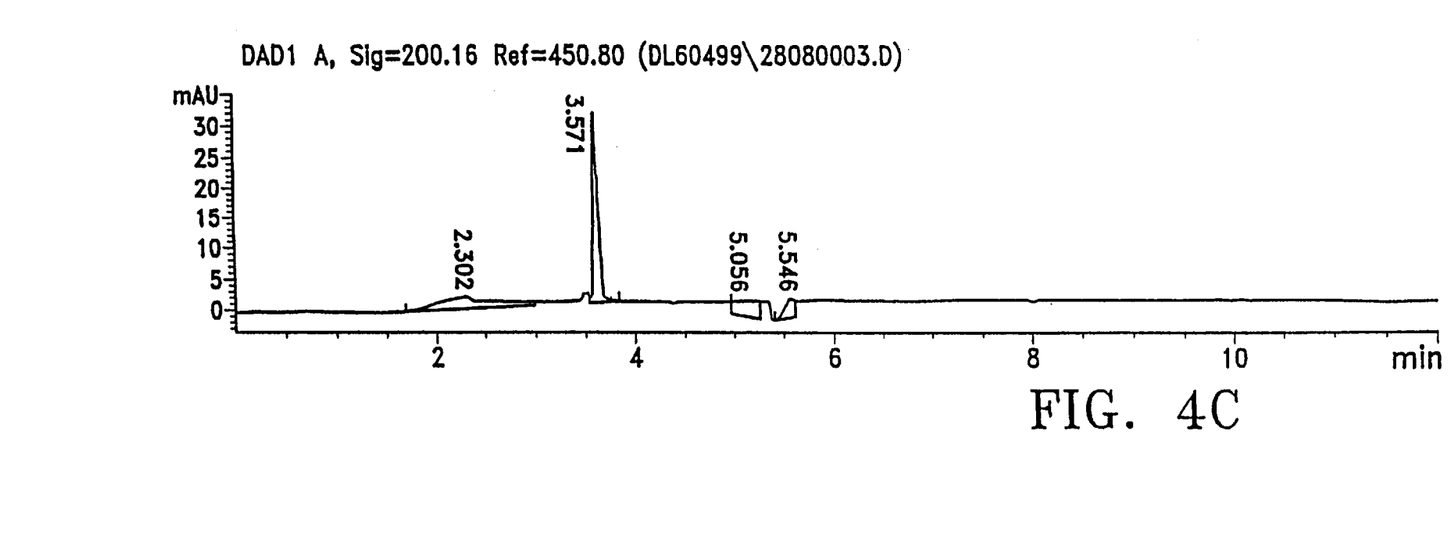
Figure 5:
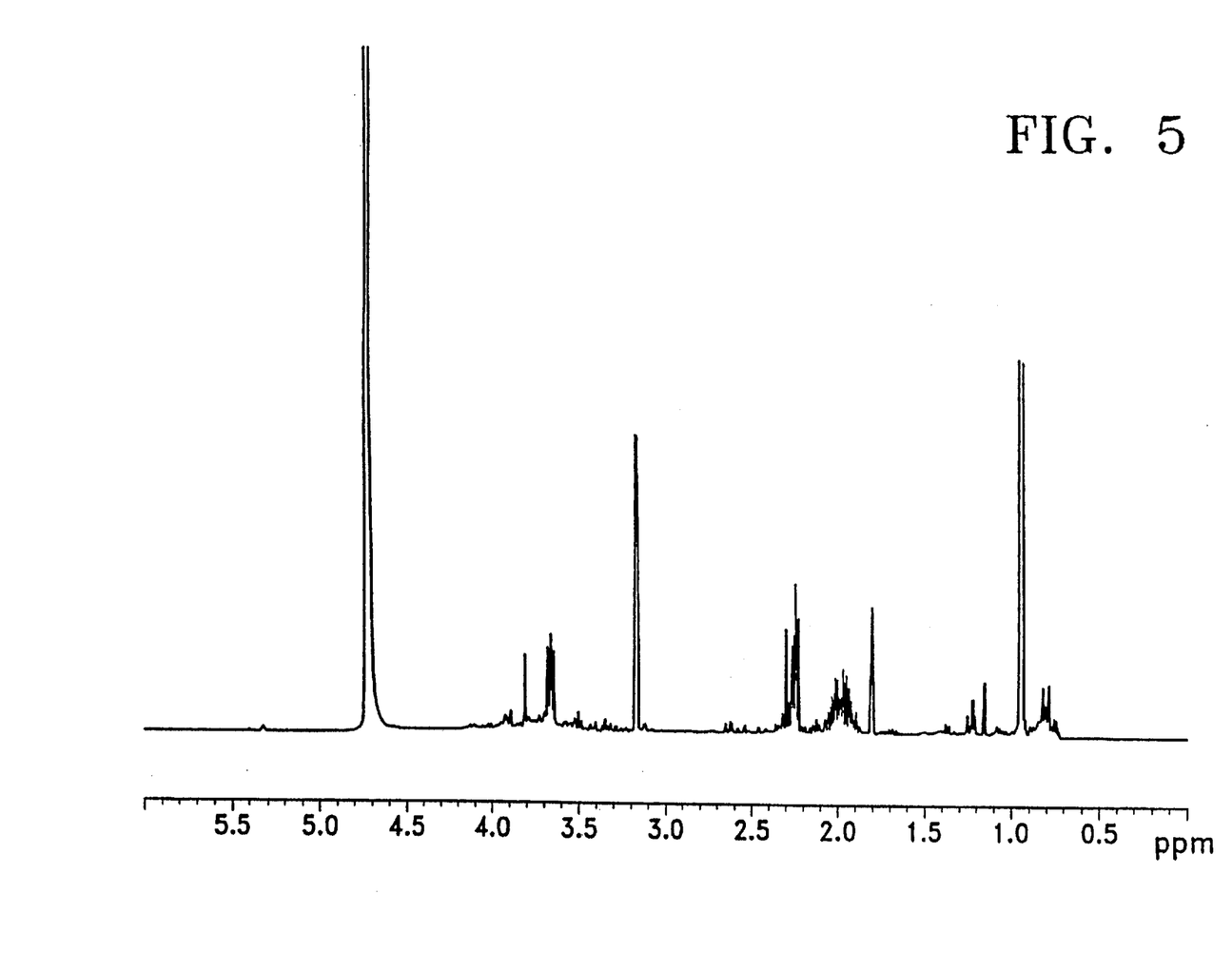
FIG. 5 shows the $^1$H NMR spectrum of the partially purified active fraction with activity as a B+ enhancer isolated from B-30087 recorded at 400 MHz in $D_2O$.

The partially-purified fractions were then compared to zwittermicin A using capillary electrophoresis (CE). FIG. 4 shows the electropherograms of the partially-purified fungicidal component of B-30087, the partially-purified fungicidal component of B-30087 spiked with 25 gl zwittermicin A and zwittermicin A alone. $^1$H-NMR spectra of zwittermicin A shown in FIG. 2, and the partially-purified fingicidal metabolite of B-30087, shown in FIG. 1, were recorded in $D_2O$ at 400 MHz. The spectra, as shown in FIGS. 1 and 2, demonstrate that the fungicidal metabolite from NRRL Accession No. B-30087 is different from zwittermicin A.

The fungicidal metabolite from NRRL Accession No. B-30087 can also be distinguished from -exotoxin by $^1$H-NMR. The $^1$H-NMR spectrum of -exotoxin has seven resonances above 5 ppm as shown in *Analytical Chemistry of Bacillus thuringiensis*, L. A. Hickle and W. L. Fitch, eds., ACS Symposium Series 432, p. 131 (1990). In contrast, FIG. 1 shows that for the NRRL Accession No. B-30087 sample, no proton resonance appears above 5 ppm.

Example 8
Purification of the Enhancer

The enhancer was semi purified from B-30087 whole broth as follows. It was semi-purified by treatment of 435 mL whole broth with anion exchange resin, acetonitrile precipitation and size exclusion chromatography. The whole broth was centrifuged to remove cells, and 14.5 g anion resin (AG 1-X8, 100–200 mesh, acetate form) was added to the supernatent and the mixture was shaken one minute. This was centrifuged at 5000 rpm, 20 minutes and the supernatant was decanted and used in the next step. Acetonitrile was added to the supernatant to give a 50% solution and it was shaken one minute and centrifuged 5000 rpm for 20 minutes. The lower dark brown layer contained the *Bacillus thuringiensis* enhancer.

The brown layer from above was further purified by size exclusion chromatography in two steps. First, 130 g of P-2 resin (BioRad) was swelled with milliQ deionized water to pack a column 2.5 cm×80 cm. The brown layer was concentrated using a rotary evaporator approximately 4× and 15 ml of the concentrate was put onto the P2 column. The column was eluted with MQ water under gravity and ten minute fractions were collected for 12 hours (UV detection at 280 nm, absorbance range 2.0, 10 mV). Further purification of fractions 26–28 was carried out by concentrating the fractions to 3× using a rotary evaporator and applying them to the original P2 column. The column was eluted with MQ water. Ten minute fractions were collected for the first 80 minutes, then 2 minute fractions were collected for the next two hours. The *Bacillus thuringiensis* enhancer activity eluted in fractions 16–20. (UV detection at 220 nm, absorbance range 2.0, 10 mV).

Example 9

Chemical Characteristics of the Enhancer are Different than Zwittermicin A

The enhancer of this invention was shown to be different than zwittermicin A on capillary electrophoresis. B-30087 whole broth was grown in a Bacillus culture media containing soy flour, dextrose, yeast extract, $KH_2PO_4$, $K_2HPO_4$, NaCl and $MgSO_{4\times7}H_2O$. Streaked cultures were used to inoculate 250 ml shake flasks. Flasks were shaken at 210 rpm at 30° C. for 4 days. *Bacillus thuringiensis* B-30087 whole broth was spiked with purified zwittermicin A and run on capillary electrophoresis (CE). 30 μL of B-30087 whole broth were spiked with 10 μL zwittermicin A. B-30087 whole broth (FIG. 3A), B-30087 whole broth plus zwittermicin A (FIG. 3B) and zwittermicin A alone (FIG. 3C) were run on the CE using sodium phosphate buffer at pH 5.8. Electropherograms of the CE are shown in FIG. 4. $^1$H-NMR spectra of zwittermicin A and B-30087 semi-purified enhancer were recorded in $D_2O$ at 400 MHz. The spectra indicate that the enhancer is different from zwittermicin A.

Example 10

Determination of Insecticidal Enhancement With *Bacillus thuringiensis*

*B. thuringiensis* enhancement was demonstrated using the whole broth of *B. pumilus*, NRRL Accession Number B-30087 by test in the beet army worm (*Spodoptera exigua*) synergy assay. Assays were performed in 96-well microplates. Each well contained a solid agar substrate. 20 μL of B-30087 whole broth was tested with a commercial preparation of *B. thuringiensis* , Javelin (0.25–1.50 μg/well) in the bioassay. A serial dilution of the Javelin concentrations alone was run as well.

To assay insecticidal activity, an agar substrate was prepared for the wells of the microplate according to Marrone et al. (1985), *J. Econ. Entomol.* 78:290–293. Deionized water was used as a negative control. Two replicates of a test sample or control were used for each assay. Plates were then placed in a fume hood to for approximately 2–3 hours to dry.

One to three *Spodoptera exigua* first instar larvae was added to each well. The microplate was sealed with an airtight substance such as Mylar®, and each well ventilated with a pin press. The plates were incubated at 27° C. for up to 7 days.

After incubation, wells were scored by noting neonate mortality or the degree of larval development. The number of dead larvae was recorded. Stunted larvae were scored with a rating from 1 to 4. Stunt score is as follows: 4=control size; 3=75% of control size; 2=50% of control size; 1=25% of control size. Results are summarized in Table 9, below.

TABLE 9

| Sample | No. dead/total | Stunt score |
|---|---|---|
| 0.25 μg Javelin | 1/8 | 4 |
| 0.50 μg Javelin | 0/8 | 4 |
| 0.75 μg Javelin | 1/8 | 2 |
| 1.0 μg Javelin | 1/8 | 2 |
| 1.50 μg Javelin | 1/8 | 2 |
| B-30087 + 0.25 μg Javelin | 3/8 | 2 |
| B-30087 + 0.50 μg Javelin | 0/8 | 3 |
| B-30087 + 1.0 μg Javelin | 7/8 | 2 |
| B-30087 + 1.50 μg Javelin | 8/8 | 1 |
| B-30087 only | 0/8 | 4 |
| Water check | 0/8 | 4 |

A second test was run using the above procedures. The results are summarized below in Table 10.

TABLE 10

| Sample | No. dead/total | Stunt score |
|---|---|---|
| 0.0625 μg Javelin | 0/8 | 4 |
| 0.125 μg Javelin | 0/8 | 4 |
| 0.187 μg Javelin | 0/8 | 4 |
| 0.250 μg Javelin | 0/8 | 3 |
| 0.375 μg Javelin | 1/8 | 2 |
| B-30087 + 0.0625 μg Javelin | 1/8 | 3 |
| B-30087 + 0.125 μg Javelin | 2/8 | 3 |
| B-30087 + 0.187 μg Javelin | 5/8 | 2 |
| B-30087 + 0.250 μg Javelin | 8/8 | 1 |
| B-30087 + 0.375 μg Javelin | 8/8 | 1 |
| B-30087 only | 0/8 | 4 |
| Water check | 0/8 | 4 |

To determine the insecticidal enhancing properties of the semi-purified fraction, the sample was tested as above using 0.1 μg/well Javelin and 40 μl/well of fractions tested. The results are shown in Table 11, below.

TABLE 11

| Sample | No. dead/total | Stunt score |
|---|---|---|
| Fraction 10 | 0/9 | 2 |
| Fraction 16 | 16/16 | 1 |
| Fraction 18 | 17/17 | 1 |
| Fraction 20 | 14/14 | 1 |
| Fraction 25 | 1/10 | 2 |
| Fraction 30 | 3/11 | 2 |
| Fraction 35 | 1/12 | 3 |
| Javelin, 0.1 μg/well | 0/8 | 3 |
| Water check | 0/14 | 4 |

Example 11
B. pumilus (B-30087) and B. subtilis (B-21661) Used Together as a Fungicide.

A strain of *B. pumilus*, NRRL B-30087 was tested with *B. subtilis*, NRRL B-21661, to determine if the fungicidal effect was greater if used together, than if each strain were used alone. Each strain was grown in a 10 liter or 5,000 liter fermenter, in a soy flour-based medium for approximately 50 hours. Each strain was tested as a whole broth culture against *Botrytis cinerea* gray mold on pepper, and *Peronospora parasitica* downy mildew on Brassica. The whole broths were tested at 1X, 1/2X and 1/8X. The two strains were then tested in various combinations with each other at 1/2X, 1/4X and 1/8X. A water check (control) and a chemical fungicide (BREAK® at 20 ppm) were also tested for comparison. The plants were scored based on a 0 to 5 scale (where 5=100% disease, no control; and 0=100% control, no disease). The results are shown in Table 12, below.

TABLE 12

|  | Botrytis cinerea Average disease rating (4 plants) | Peronospora parasitica Average disease rating (4 plants) |
|---|---|---|
| B-21661 1X | 0.3 | Not tested |
| 1/2X | 0.3 | 0.5 |
| 1/4X | 1.2 | 1.0 |
| 1/8X | 1.7 | 2.0 |
| B-30087 1X | 1.7 | Not tested |
| 1/2X | 2.3 | 1.3 |
| 1/4X | Not tested | 3.7 |
| 1/8X | Not tested | 4.3 |
| B-21661 1/4X and B-30087 1/2X | 0.7 | 1.0 |
| B-21661 1/8X and B-30087 1/2X | 1.4 | 0.3 |
| B-21661 1/4X and B-30087 1/4X | N/A | 0.5 |
| B-21661 1/2X and B-30087 1/2X | N/A | 0.3 |
| B-21661 1/2X and B-30087 1/4X | N/A | 0.3 |
| B-21661 1/2X and B-30087 1/8X | N/A | 0.5 |
| BREAK ® at 20 ppm | 0.2 | Not tested |
| Water check | 4.6 | 5.0 |

The *Botrytis cinerea* test results show statistical differences when the strains are used in combination compared to when they are used alone. For example, the score of 0.7 for B-21661 1/4X and B-30087 1/2X is statistically different than the score of 1.2 for B-21661 1/4X used alone. Also, the score of 1.4 for B-21661 1/8X and B-30087 1/2X is statistically different than the score of 1.7 for B-21661 1/8X alone or 2.3 for B-30087 1/2X alone, and the score together is lower than the expected average for each strain used alone. This shows the synergistic effect of using the strains together for increased efficacy as a fingicide.

The *Peronospora parasitica* test results show the score for the combination of B-21661 1/8X and B-30087 1/2X was far better than would be expected from an additive effect. A score of 2.05 would be expected if there were only an additive effect from the combination of strains. However, the actual score was 0.3, showing that there is a definite synergistic effect by using the strains in combination. Other scores also show better than expected results, for example, the B-21661 1/4X and B-30087 1/4X has a score of 0.5, which is much better than would be expected from only an additive effect (estimated score of 2.35) of the individual strains. This same synergy is also shown in the combinations of B-21661 1/2X and B-30087 1/2X (score of 0.3), B-21661 1/2X and B-30087 1/4X (score of 0.3), and B-21661 1/2X and B-30087 1/8X (score of 0.5). These tests prove there is a synergistic effect when using the strains in combination, and is an unexpected result.

It is to be understood that while the invention has been described in conjunction with the above embodiments, that the foregoing description and the examples are intended to illustrate and not limit the scope of the invention. Other aspects, advantages and modifications within the scope of the invention will be apparent to those skilled in the art to which the invention pertains.

What is claimed is:

1. A composition for treating a fungal infection in a plant, root or fruit comprising a combination of:
    a) an effective amount of a whole broth culture of a strain having all the identifying characteristics of a *Bacillus pumilus* strain designated NRRL Accession No. B-30087, or mutants thereof that have fungicidal activity and
    b) an effective amount of a wbole broth culture of a strain having all the identiying characteristics of a *Bacillus subtilis* strain designated NRRL Accession No. B-21661, or mutants thereof that have fungicidal activity.

2. The composition of claim 1, wherein the fungicidal activity is against *Botrytis cinerea* and *Peronospora parasitica*.

3. A method for treating a fungal infection in a plant, root or fruit comprising applying an effective amount of the composition of claim 2 to said plant, root or fruit to treat said fungal infection.

4. A method for treating a fungal infection in a plant, root or fruit comprising applying an effective amount of the composition of of claim 1 to said plant, root or fruit to treat said fungal infection.

5. The composition of claim 1, further comprising at least one biological or chemical pesticide.

6. The composition of claim 5, wherein the composition is formulated as a wettable powder, a granule, an aqueous suspension, an emulsion, or as a microencapsulated particle.

7. A method for preventing or treating a plant, root or fruit from a fungal infection comprising applying an effective amount of the composition of claim 5.

8. A composition for treating a fungal infection in a plant, root or fruit comprising a combination of:
    a) an effective amount of a whole broth culture of a strain having all the identifying characteristics of a *Bacillus pumilus* strain designated NRRL Accession No. B-30087, or mutants thereof that have fungicidal activity and
    b) an effective amount of a whole broth culture of a strain having all the identifying characteristics of a *Bacillus subtilis* strain designated NRRL Accession No. B-21661, or mutants thereof that have fungicidal activity, wherein the combination of (a) and (b) has synergistic fungicidal activity when combined in a ratio of 2:1.

9. The composition of claim 8, further comprising at least one biological or chemical pesticide.

10. A method for treating a fungal infection in a plant, root or fruit comprising applying an effective amount of the composition of claim 8 to said plant, root or fruit to treat said fungal infection.

11. A method for treating a fungal infection in a plant, root or fruit by *Botytis cinerea* or *Peronospora parasitica* comprising applying an effective amount of the composition of claim 8 to said plant, root or fruit to treat said fungal infection.

12. A composition for treating a fungal infection in a plant, root or fruit comprising a combination of:
    a) an effective amount of a whole broth culture of a strain having all the identifying characteristics of a *Bacillus*

*pumilus* strain designated NRRL Accession No. B-30087, or mutants thereof that have fungicidal activity and b) an effective amount of a whole broth culture of a strain having all the identifying characteristics of a *Bacillus subtilis* strain designated NRRL Accession No. B-21661, or mutant thereof that have fungicidal activity, wherein the combination of (a) and (b) has synergistic fingicidal activity when combined in a ratio of about 4:1.

13. The composition of claim 12, further comprising at least one biological or chemical pesticide.

14. A method for treating a fungal infection in a plant, root or fruit comprising applying an effective amount of the composition of claim 12 to said plant, root or fruit to treat said fungal infection.

15. A method for treating a fungal infection in a plant, root or fruit by *Botytis cinerea* or *Peronospora parasitica* comprising applying an effective amount of the composition of claim 12 to said plant, root or fruit to treat said fungal infection.

* * * * *